(12) United States Patent
Watanabe et al.

(10) Patent No.: US 9,910,140 B2
(45) Date of Patent: Mar. 6, 2018

(54) ULTRASONIC MEASUREMENT APPARATUS, ULTRASONIC IMAGING APPARATUS, AND ULTRASONIC MEASUREMENT METHOD

(71) Applicant: SEIKO EPSON CORPORATION, Tokyo (JP)

(72) Inventors: Ryoki Watanabe, Nagano (JP); Masaki Hayashi, Nagano (JP); Kazuyuki Kano, Aichi (JP); Kenji Murakami, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 514 days.

(21) Appl. No.: 14/474,796

(22) Filed: Sep. 2, 2014

(65) Prior Publication Data
US 2015/0063058 A1    Mar. 5, 2015

(30) Foreign Application Priority Data

Sep. 5, 2013   (JP) ................................. 2013-183798
Jun. 25, 2014   (JP) ................................. 2014-129971

(51) Int. Cl.
*A61B 8/00*       (2006.01)
*G01S 7/52*       (2006.01)
*G01S 15/89*      (2006.01)

(52) U.S. Cl.
CPC ........ *G01S 7/52017* (2013.01); *A61B 8/4494* (2013.01); *G01S 7/52047* (2013.01); *G01S 7/52063* (2013.01); *G01S 15/8915* (2013.01)

(58) Field of Classification Search
USPC ......................................................... 367/11
See application file for complete search history.

(56) References Cited

U.S. PATENT DOCUMENTS 5,485,561 A   1/1996   Iizuka et al.
6,077,226 A   6/2000   Washburn et al.
(Continued)

FOREIGN PATENT DOCUMENTS

JP   2011-005237 A   1/2011
JP   2011-217998 A   11/2011
(Continued)

OTHER PUBLICATIONS

Hoskins, Peter R., Kevin Martin, and Abigail Thrush, eds. Diagnostic ultrasound: physics and equipment. Cambridge University Press, 2010.*
(Continued)

*Primary Examiner* — Isam A Alsomiri
*Assistant Examiner* — Jonathan D Armstrong
(74) *Attorney, Agent, or Firm* — Global IP Counselors, LLP

(57) ABSTRACT

Provided are an ultrasonic measurement apparatus, an ultrasonic imaging apparatus and an ultrasonic measurement method that achieve an increase in processing speed together with an increase in resolution and are user friendly. An image is generated by adding together, with a weight having a fixed value, reception signals obtained by ultrasonic echoes being received by an ultrasonic element array, and an area of interest is set within the area in which the generated image is to be displayed. When an area of interest is acquired, the reception signals received by the ultrasonic element array are added together with weights that depend on the reception signals, with respect to data forming the basis of the image to be displayed in the area of interest, and image generation is performed.

11 Claims, 15 Drawing Sheets

(56) References Cited

U.S. PATENT DOCUMENTS

| | | | | |
|---|---|---|---|---|
| 6,142,942 A * | 11/2000 | Clark | ............... | G01S 7/52025 600/443 |
| 7,430,257 B1 * | 9/2008 | Shattil | ............... | H04B 1/707 342/367 |
| 8,600,299 B2 * | 12/2013 | Randall | ............... | A61B 8/00 128/916 |
| 2005/0033168 A1 * | 2/2005 | Shifrin | ............... | G01S 7/52017 600/437 |
| 2005/0195103 A1 * | 9/2005 | Davis | ............... | H01Q 21/22 342/99 |
| 2005/0283074 A1 * | 12/2005 | Jackson | ............... | A61B 18/1492 600/439 |
| 2007/0161904 A1 * | 7/2007 | Urbano | ............... | A61B 8/00 600/459 |
| 2007/0285315 A1 * | 12/2007 | Davis | ............... | G01S 3/74 342/377 |
| 2008/0110263 A1 * | 5/2008 | Klessel | ............... | G01S 7/52028 73/602 |
| 2008/0114239 A1 * | 5/2008 | Randall | ............... | G01S 7/52073 600/437 |
| 2009/0190814 A1 * | 7/2009 | Bouman | ............... | G06T 11/006 382/131 |
| 2009/0316141 A1 * | 12/2009 | Feldkhun | ............... | G01N 21/6458 356/217 |
| 2012/0022373 A1 | 1/2012 | Tateyama | | |
| 2012/0289835 A1 * | 11/2012 | Hwang | ............... | G01S 7/52047 600/447 |
| 2012/0314534 A1 | 12/2012 | Yoda et al. | | |
| 2013/0116538 A1 * | 5/2013 | Herzog | ............... | A61B 8/4254 600/407 |
| 2013/0184587 A1 * | 7/2013 | Eom | ............... | A61B 8/4411 600/443 |
| 2015/0063057 A1 * | 3/2015 | Hayashi | ............... | A61B 8/56 367/7 |

FOREIGN PATENT DOCUMENTS

| | | | | |
|---|---|---|---|---|
| WO | WO 2008108115 A1 * | 9/2008 | ......... | A61B 8/4483 |
| WO | 2010/137453 A1 | 12/2010 | | |
| WO | 2012/153481 A1 | 11/2012 | | |

OTHER PUBLICATIONS

Synnevag, Johan-Fredrik, Andreas Austeng, and Sverre Holm. "Benefits of minimum-variance beamforming in medical ultrasound imaging." IEEE transactions on ultrasonics, ferroelectrics, and frequency control 56.9 (2009): 1868-1879.*

* cited by examiner

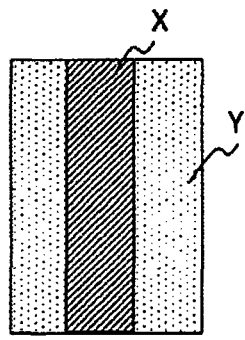 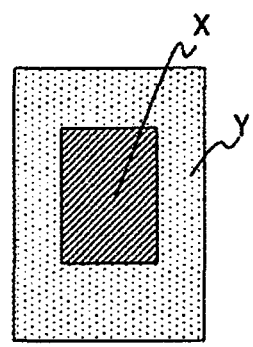
FIG.10A  FIG.10B
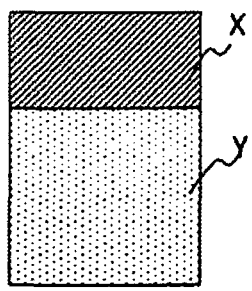 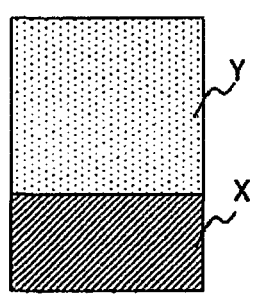
FIG.10C  FIG.10D
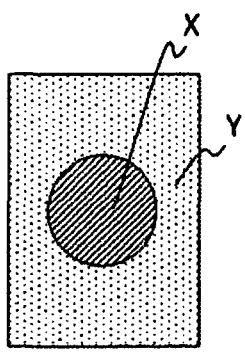 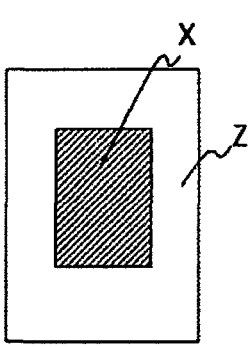
FIG.10E  FIG.10F

ULTRASONIC MEASUREMENT APPARATUS, ULTRASONIC IMAGING APPARATUS, AND ULTRASONIC MEASUREMENT METHOD

BACKGROUND

1. Technical Field

The present invention relates to an ultrasonic measurement apparatus, an ultrasonic imaging apparatus, and an ultrasonic measurement method.

2. Related Art

JP-A-2011-5237 discloses that high speed signal processing is possible by providing a signal conversion unit that converts analog signals into digital signals, an operation unit that performs adaptive signal processing on the digital signals and generates image information, and a data thinning unit that reduces the data volume of the digital signals to be transferred from the signal conversion unit to the operation unit in a measurement apparatus for generating image data of the inside of a subject using analog signals obtained by ultrasonic waves that have propagated through the subject being received by a plurality of ultrasonic conversion elements.

JP-A-2011-217998 discloses an acoustic wave imaging apparatus having a phasing unit that aligns the phases of reception signals of a plurality of acoustic wave receiving elements, a complex signal conversion unit that converts the reception signals with aligned phases into complex signals, a correlation matrix calculation unit that calculates a correlation matrix of the complex signals, and a power calculation unit that calculates a constrained minimum electric power of the reception signals using the correlation matrix and a predetermined constraint vector, in which the correlation matrix calculation unit calculates the correlation matrix at a predetermined cycle and outputs the calculated correlation matrices to the power calculation unit sequentially, and the power calculation unit performs constrained minimum power calculations in parallel using the respective correlation matrices that are input.

The invention disclosed in JP-A-2011-5237 involves thinning the data to speed up the calculation processing by adding together the digital signals of adjacent elements, although there is a problem in that this unavoidably leads to a certain degree of degradation in image quality.

The invention disclosed in JP-A-2011-217998 proposes a method for improving the calculation speed by providing a plurality of storage circuits and calculation circuits and performing operations in parallel, although there is a problem in that circuit size and power consumption increase, and heat generation becomes an issue.

SUMMARY

An advantage of some aspects of the invention is to provide an ultrasonic measurement apparatus, an ultrasonic imaging apparatus and an ultrasonic measurement method that achieve an increase in processing speed together with an increase in resolution and are user friendly.

An ultrasonic measurement apparatus according to a first aspect of the invention includes an image processing unit that generates an image based on a reception signal obtained by an ultrasonic echo of an ultrasonic wave transmitted toward an object from an ultrasonic element array provided with a plurality of channels being received by the ultrasonic element array, and an area-of-interest setting unit that sets an area of interest within an area in which the generated image is to be displayed. The image processing unit, when the area of interest is set, adds together the reception signals of respective channels among the plurality of channels with a weight that depends on the reception signals of the respective channels, with respect to data forming a basis of an image to be displayed in the area of interest, and performs image generation based on the reception signal obtained from the adding.

According to the first aspect, an image is generated based on reception signals obtained by ultrasonic echoes being received by an ultrasonic element array, and an area of interest is set within the area in which the generated image is to be displayed. When an area of interest is acquired, the reception signals of the respective channels are added together with weights that depend on the reception signals, with respect to data forming the basis of the image to be displayed in the area of interest, and image generation is performed. An increase in processing speed can thereby be achieved together with an increase in resolution, and usability can be improved.

Here, the weight that depends on the reception signal of each channel may be derived so as to minimize a variance of a result of multiplying the output signal of the channel after a delay time that depends on a linear distance from an object to the channel by the weight that depends on the reception signal of the channel. The problem of a decrease in azimuth resolution can thereby be remedied, since a directional constraint is applied so as to not have sensitivity to unwanted waves.

When the area of interest is set, the reception signals of respective channels among the plurality of channels may be added together with a weight that depends on the reception signals of the respective channels, with respect to data forming a basis of an image to be displayed in the area of interest, and image generation may be performed based on the reception signal obtained from the adding. An increase in processing speed can thereby be achieved together with an increase in resolution, and usability can be improved.

Here, an area input unit that receives input of an arbitrary point or area on an image displayed on the display unit may be provided, and the area-of-interest setting unit may set the area of interest based on the arbitrary point or area that was input. The user is thereby able to select the position, size, shape and the like of the area of interest.

Here, the area input unit may receive input of a desired frame rate, and the area-of-interest setting unit may set the area of interest to a size that enables image generation at a frame rate at or above the desired frame rate. The user is thereby able to generate images at an arbitrary frame rate.

Here, the area-of-interest setting unit may set a rectangular, trapezoidal or fan-shaped area as the area of interest, and may specify the rectangular, trapezoidal or fan-shaped area using coordinates of four corners. An area of interest having a shape that depends on the configuration of the ultrasonic element array (for example, an ultrasonic element array compatible with linear scanning, an ultrasonic element array compatible with convex scanning, etc.) can thereby be set.

Here, the area-of-interest setting unit may set a circular or elliptical area as the area of interest, and may specify the circular or elliptical area using center coordinates and a diameter. The smallest possible area of interest can thereby be set.

Here, the display unit may display information showing the set area of interest so as to be overlaid on the generated image or instead of the generated image, the area input unit may receive input for changing the information showing the area of interest, and the area-of-interest setting unit may set the area of interest based on the information showing the area of interest with respect to which the change input was received. The size of the image and the size of the area of interest can thereby be compared, and the user is able to easily select the position, size, shape, and the like of the area of interest.

Here, a phasing and adding circuit that adds together the acquired reception signals with a weight computed in advance with respect to data other than the data forming a basis of the image to be displayed in the area of interest may be provided. Any sense of strangeness felt when viewing the image can thereby be reduced.

An ultrasonic measurement method according to a second aspect of the invention involves generating an image based on a reception signal obtained by an ultrasonic echo of an ultrasonic wave transmitted toward an object being received, setting an area of interest within an area in which the generated image is to be displayed, and adding together, when the area of interest is set, the reception signals with a weight that depends on the reception signals, with respect to data forming a basis of an image to be displayed in the area of interest, and performing image generation based on the reception signal obtained from the adding. An increase in processing speed can thereby be achieved together with an increase in resolution, and usability can be improved.

BRIEF DESCRIPTION OF THE DRAWINGS

The invention will be described with reference to the accompanying drawings, wherein like numbers reference like elements.

FIGS. 10A to 10F show modes of the area of interest.

DESCRIPTION OF EXEMPLARY EMBODIMENTS

Embodiments of the invention will now be described with reference to the drawings.

Figure 1:
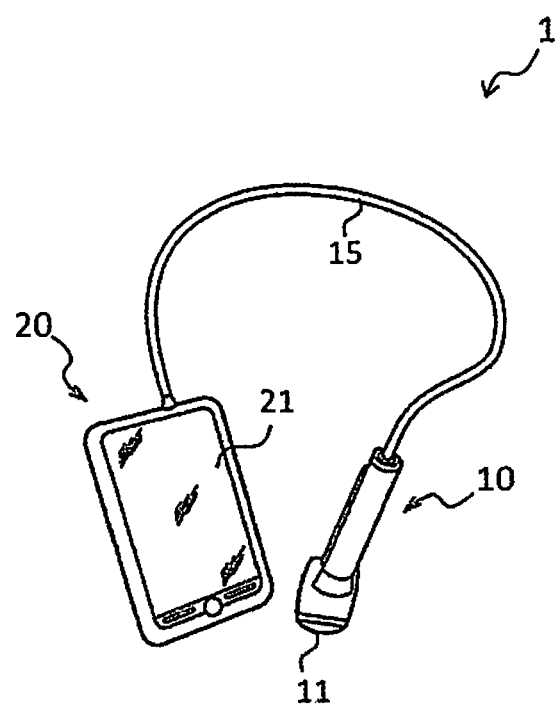
FIG. 1 is a perspective diagram showing a schematic configuration of an ultrasonic imaging apparatus 1 according to a first embodiment of the invention.

FIG. 1 shows a general view of an ultrasonic imaging apparatus 1 according to a first embodiment of the invention. The ultrasonic imaging apparatus 1 is, for example, a compact ultrasonic measurement apparatus. The ultrasonic imaging apparatus 1 primarily includes an ultrasonic probe 10 and an ultrasonic measurement apparatus main body 20, with the ultrasonic probe 10 and the ultrasonic measurement apparatus main body 20 being connected by a cable 15. Note that the ultrasonic imaging apparatus 1 is not limited to being a compact ultrasonic measurement apparatus, and may be, for example, a stationary ultrasonic measurement apparatus, or an integrated ultrasonic measurement apparatus in which the ultrasonic probe is built into the main body.

Also, the ultrasonic imaging apparatus 1 uses an ultrasonic element array that is compatible with linear scanning and sector scanning, and employs electronic focusing. In the case of linear scanning, the aperture is divided, and lines are generated while performing transmission and reception with the resultant apertures. In the case of sector scanning, the full aperture is used, and lines are generated while changing the beam direction. Hereinafter, the case where the ultrasonic imaging apparatus 1 performs linear scanning will be described as an example.

The ultrasonic probe 10 has an ultrasonic transducer device 11. The ultrasonic transducer device 11 transmits an ultrasonic beam toward an object while scanning over the object along a scan plane, and receives ultrasonic echoes of the ultrasonic beam.

Taking a type that uses piezoelectric elements as an example, the ultrasonic transducer device 11 has a plurality of ultrasonic transducer elements 12 (ultrasonic element array; refer to FIG. 2, etc.) and a substrate in which a plurality of apertures are disposed in an array.

Figure 2A:
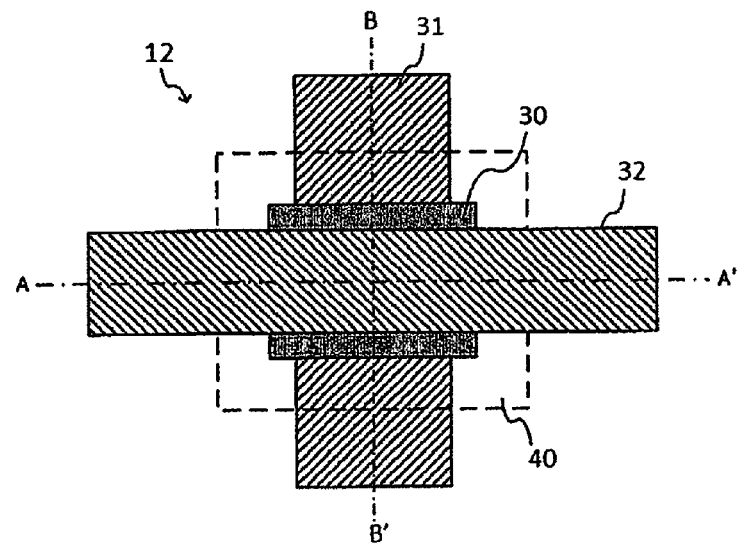
FIGS. 2A to 2C show an exemplary schematic configuration of an ultrasonic transducer element.
Figure 2B:
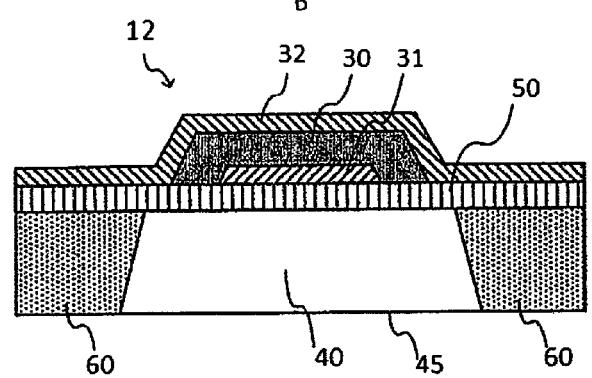
Figure 2C:
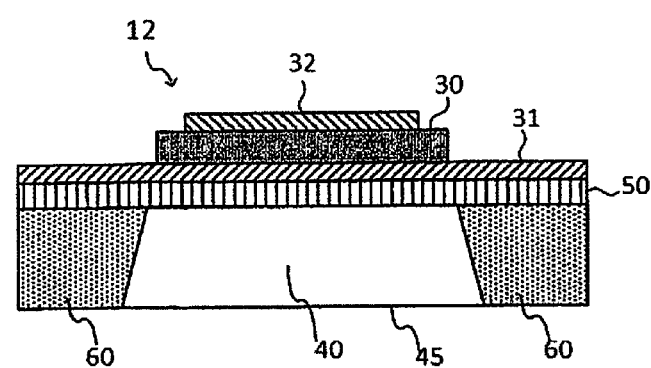

FIGS. 2A to 2C show an exemplary configuration of the ultrasonic transducer elements 12 of the ultrasonic transducer device 11. In the present embodiment, a monomorph (unimorph) structure in which a thin piezoelectric element and a metal plate (vibration film) are stuck together is employed as the ultrasonic transducer elements 12.

FIGS. 2A to 2C show an exemplary configuration of the ultrasonic transducer elements 12 of the ultrasonic transducer device 11. FIG. 2A is a plan view of an ultrasonic transducer element 12 formed on a substrate (silicon substrate) 60 viewed from an element formation side in a direction perpendicular to a substrate 60. FIG. 2B is a cross-sectional view showing a cross-section along A-A' in FIG. 2A. FIG. 2C is a cross-sectional view showing a cross-section along B-B' in FIG. 2A.

The ultrasonic transducer element 12 has a piezoelectric element part and a vibration film (membrane, supporting member) 50. The piezoelectric element part primarily includes a piezoelectric layer (piezoelectric film) 30, a first electrode layer (lower electrode) 31, and a second electrode layer (upper electrode) 32.

The piezoelectric layer 30 is formed using a PZT (lead zirconate titanate) thin film, for example, and is provided so as to cover at least a portion of the first electrode layer 31. Note that the material of the piezoelectric layer 30 is not limited to PZT, and materials such as lead titanate ($PbTiO_3$), lead zirconate ($PbZrO_3$) and lead lanthanum titanate ($(Pb, La)TiO_3$), for example, may be used.

The first electrode layer 31 is formed on an upper layer of the vibration film 50 with a metal thin film, for example. This first electrode layer 31 may be an interconnect that extends to outside the element formation area as shown in FIG. 2A, and is connected to an adjacent ultrasonic transducer element 12.

The second electrode layer 32 is formed with a metal thin film, for example, and is provided so as to cover at least a portion of the piezoelectric layer 30. This second electrode layer 32 may be an interconnect that extends to outside the element formation area as shown in FIG. 2A, and is connected to an adjacent ultrasonic transducer element 12.

The lower electrode of the ultrasonic transducer element 12 is formed by the first electrode layer 31, and the upper electrode is formed by the second electrode layer 32. Specifically, the portion of the first electrode layer 31 covered by the piezoelectric layer 30 forms the lower electrode, and the portion of the second electrode layer 32 covering the piezoelectric layer 30 forms the upper electrode. That is, the piezoelectric layer 30 is provided so as to be sandwiched between the lower electrode and the upper electrode.

An aperture 40 is formed by etching such as reactive ion etching (RIE) or the like from the back surface (surface on which the element is not formed) side of the substrate 60. The resonance frequency of ultrasonic waves is determined by the size of the aperture 40, and the ultrasonic waves are emitted to the piezoelectric layer 30 side (in a direction from far to near in FIG. 2A).

The vibration film 50 is provided so as to block the aperture 40 using a two layer structure consisting of a $SiO_2$ thin film and a $ZrO_2$ thin film, for example. This vibration film 50 supports the piezoelectric layer 30 and the first and second electrode layers 31 and 32, and produces ultrasonic waves by vibrating in accordance with the expansion and contraction of the piezoelectric layer 30.

Figure 3:
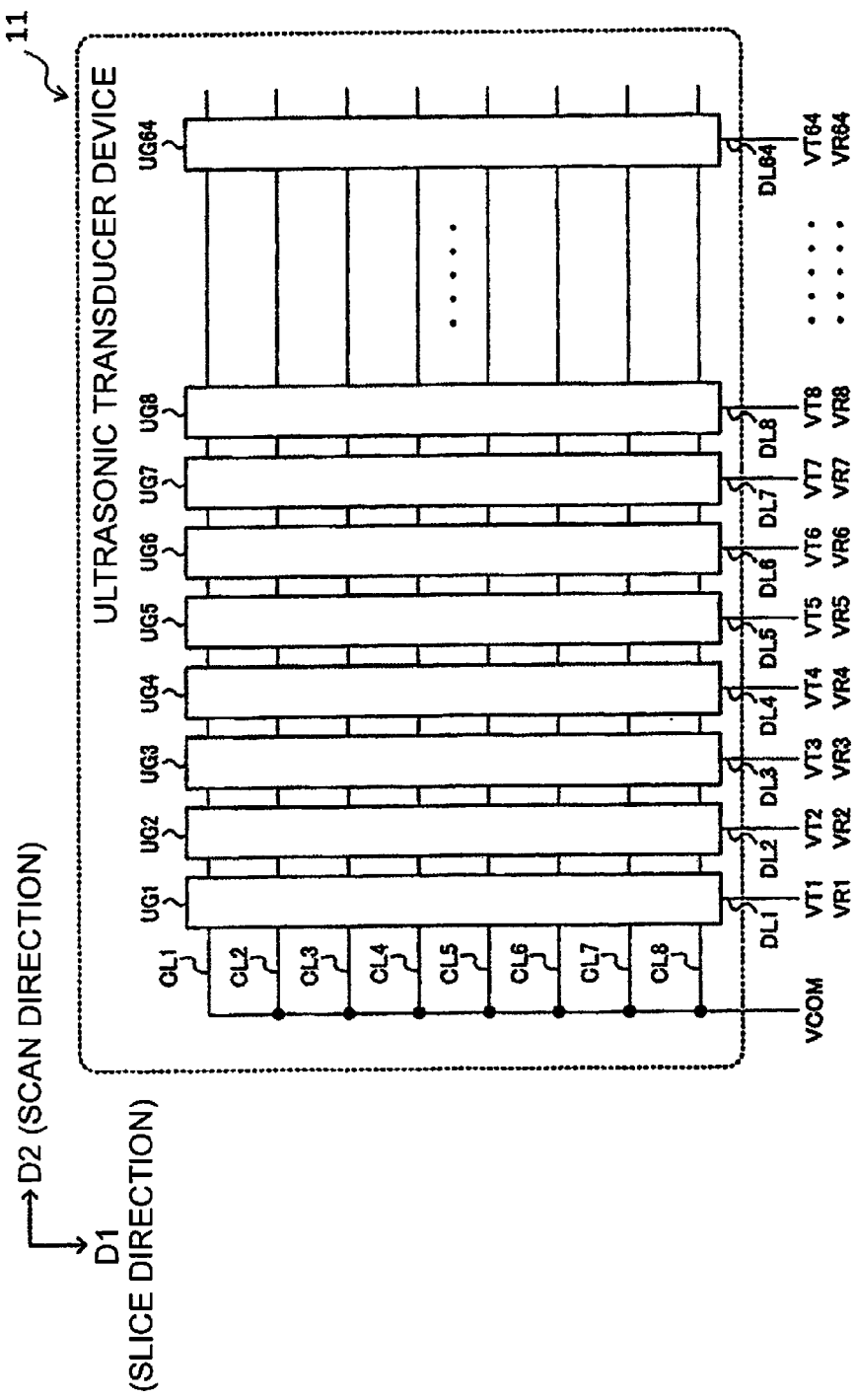
FIG. 3 shows an exemplary configuration of an ultrasonic transducer device (element chip).

FIG. 3 shows an exemplary configuration of the ultrasonic transducer device (element chip). The ultrasonic transducer device having this exemplary configuration includes a plurality of ultrasonic transducer element groups UG1 to UG64 and drive electrode lines DL1 to DL64 (broadly, 1st to mth drive electrode lines, where m is an integer of 2 or more) and common electrode lines CL1 to CL8 (broadly, 1st to nth common electrode lines, where n is an integer of 2 or more). Note that the number (m) of drive electrode lines and the number (n) of common electrode lines are not limited to the numbers shown in FIG. 3.

The plurality of ultrasonic transducer element groups UG1 to UG64 are disposed in 64 columns in a second direction D2 (scan direction). Each of the ultrasonic transducer element groups UG1 to UG64 has a plurality of ultrasonic transducer elements that are disposed in a first direction D1 (slice direction).

Figures 4A, 4B:
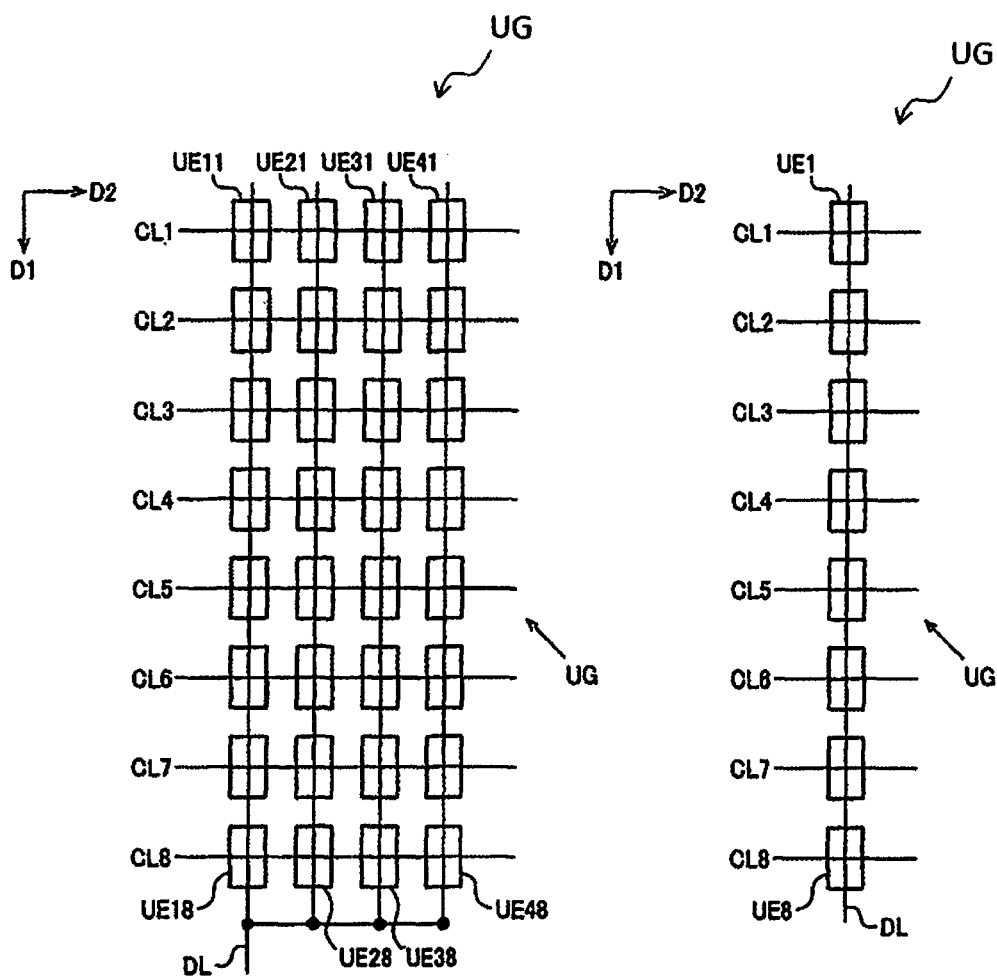
FIGS. 4A and 4B show exemplary ultrasonic transducer element groups UG (UG1 to UG64), with FIG. 4A showing the case where there are four element columns, and FIG. 4B showing the case where there is one element column.

FIG. 4A shows an exemplary ultrasonic transducer element group UG (UG1 to UG64). In FIG. 4A, the ultrasonic transducer element group UG is constituted by first to fourth element columns. The first element column is constituted by ultrasonic transducer elements UE11 to UE18 that are disposed in the first direction D1, and the second element column is constituted by ultrasonic transducer elements UE21 to UE28 that are disposed in the first direction D1. The third element column (UE31 to UE38) and the fourth element column (UE41 to UE48) are also similarly constituted. The drive electrode line DL (DL1 to DL64) is commonly connected to the first to fourth element columns. Also, the common electrode lines CL1 to CL8 are connected to the ultrasonic transducer elements of the first to fourth element columns.

The ultrasonic transducer element group UG in FIG. 4A constitutes one channel of the ultrasonic transducer device. That is, the drive electrode line DL is equivalent to the drive electrode line of one channel, and the transmission signal of one channel from a transmission circuit is input to the drive electrode line DL. Also, the reception signal of one channel constituted by the ultrasonic transducer element group UG is output from the drive electrode line DL. Note that the number of element columns constituting one channel is not limited to four columns as shown in FIG. 4A, and may be less than four columns or greater than four columns. For example, one channel may be constituted by a single element column, as shown in FIG. 4B.

Returning to the description of FIG. 3, the drive electrode lines DL1 to DL64 (1st to mth drive electrode lines) are laid in the first direction D1. An ith drive electrode line DLi among the drive electrode lines DL1 to DL64 (where i is an integer such that $1 \leq i \leq m$) is connected to the lower electrode of the ultrasonic transducer elements UE of the ith ultrasonic transducer element group UGi.

Transmission signals VT1 to VT64 are supplied to the ultrasonic transducer elements UE via the drive electrode lines DL1 to DL64 in a transmission period for emitting ultrasonic waves. Also, reception signals VR1 to VR64 from the ultrasonic transducer elements UE are output via the drive electrode lines DL1 to DL64 in a reception period for receiving ultrasonic echo signals.

The common electrode lines CL1 to CL8 (1st to nth common electrode lines) are laid in the second direction D2. The second electrode of the ultrasonic transducer elements UE is connected to one of the common electrode lines CL1 to CL8. Specifically, as shown in FIG. 3, for example, a jth common electrode line CLj (where j is an integer such that $1 \leq j \leq n$) among the common electrode lines CL1 to CL8 is connected to the upper electrode of the ultrasonic transducer elements that are disposed in the jth line.

A common voltage $V_{COM}$ is supplied to the common electrode lines CL1 to CL8. This common voltage $V_{COM}$ need only be a constant direct current voltage, and not 0V, that is, not ground potential.

In the transmission period, a difference voltage between the transmission signal voltage and the common voltage is applied to the ultrasonic transducer elements UE, and ultrasonic waves of a predetermined frequency are emitted.

Note that the arrangement of the ultrasonic transducer elements UE is not limited to the matrix arrangement shown in FIG. 3, and may be in a so-called houndstooth arrangement in which the elements of any two adjacent columns are disposed so as to zigzag alternately. Also, in FIGS. 4A and 4B, the case is shown where a single ultrasonic transducer element is used as both a transmission element and a reception element, but the present embodiment is not limited thereto. For example, ultrasonic transducer elements for use as transmission elements and ultrasonic transducer elements for use as reception elements may be provided separately, and disposed in an array.

Also, the ultrasonic transducer elements 12 are not limited to a configuration which uses piezoelectric elements. For example, transducers that use capacitive elements, such as capacitive micro-machined ultrasonic transducers (cMUTs) may be employed, or bulk transducers may be employed.

Returning to the description of FIG. 1, a display unit 21 is provided in the ultrasonic measurement apparatus main body 20. The display unit 21 displays image data for display generated by an image processing unit 130 (refer to FIG. 5).

A liquid crystal display, an organic electroluminescence display or electronic paper, for example, can be used for the display unit 21.

Figure 5:
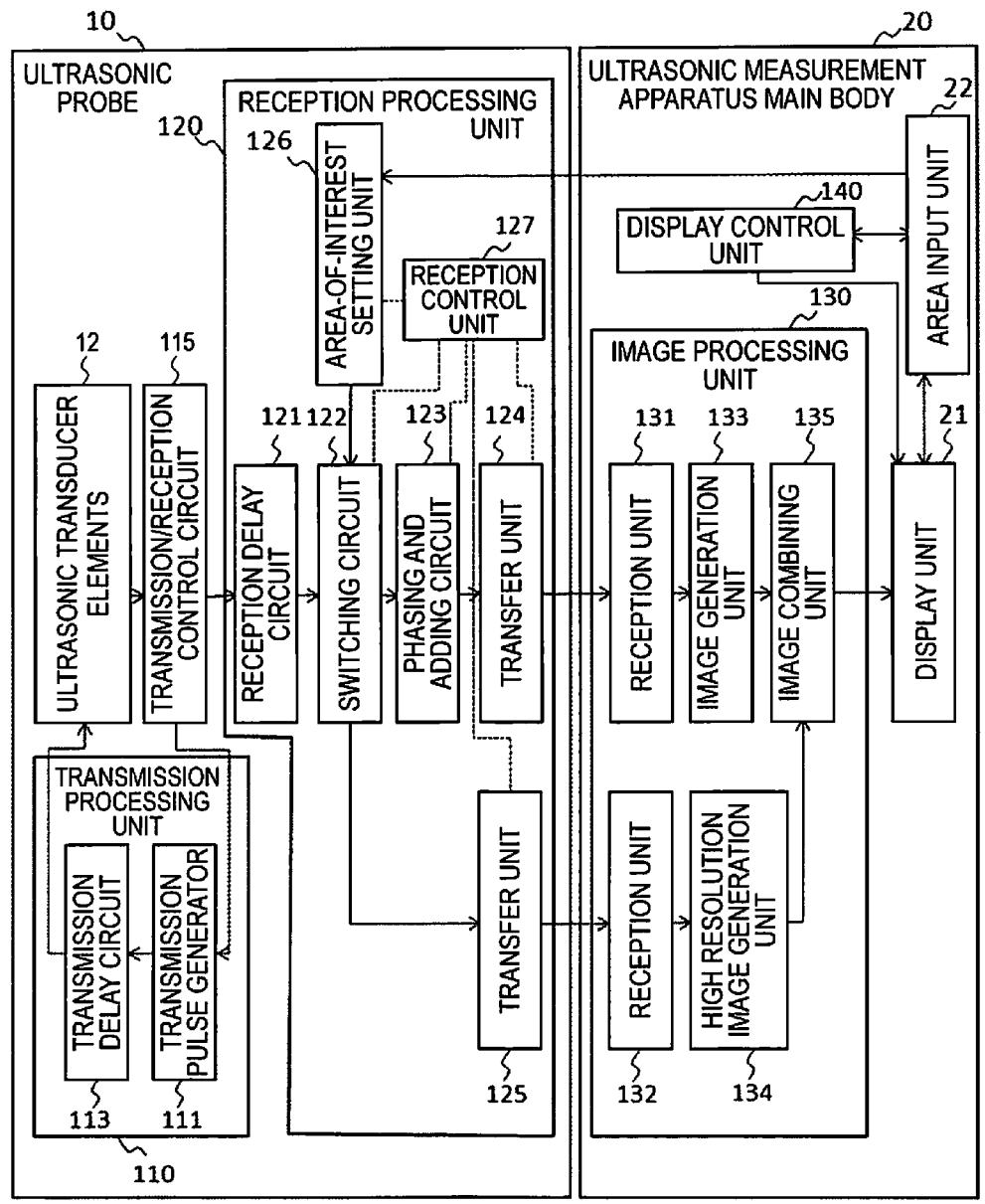
FIG. 5 is a block diagram showing an exemplary functional configuration of the ultrasonic imaging apparatus 1.

FIG. 5 is a block diagram showing an exemplary functional configuration of the ultrasonic imaging apparatus 1. The ultrasonic probe 10 is primarily provided with a transmission processing unit 110, a transmission/reception control circuit 115, and a reception processing unit 120. The ultrasonic measurement apparatus main body 20 is primarily provided with the image processing unit 130 and a display control unit 140. Note that, in the present embodiment, the reception processing unit 120 is provided in the ultrasonic probe 10, but may be provided in the ultrasonic measurement apparatus main body 20.

The transmission processing unit 110 performs processing for transmitting ultrasonic waves toward an object from the ultrasonic transducer elements 12. The transmission processing unit 110 includes a transmission pulse generator 111 and a transmission delay circuit 113.

The transmission pulse generator 111 applies a transmission pulse voltage to drive the ultrasonic transducer elements 12.

The transmission delay circuit 113 performs transmission focusing control, and the ultrasonic transducer elements 12 emit an ultrasonic beam corresponding to the generated pulse voltage toward the object. Thus, the transmission delay circuit 113 provides a time difference between channels with regard to the application timing of the transmission pulse voltage, and causes the ultrasonic waves produced by the plurality of vibration elements to converge. It is thus possible to arbitrarily change the focal length by changing the delay time.

The transmission/reception control circuit 115 controls the transmission processing unit 110, and causes ultrasonic waves to be transmitted from the ultrasonic transducer elements 12 toward the object at a predetermined frame rate. The predetermined frame rate may be input by the user from an area input unit 22 (discussed in detail later), or may be computed by the area-of-interest setting unit 126 (discussed in detail later).

Also, the transmission/reception control circuit 115 performs processing for changing over transmission/reception of ultrasonic waves. The transmission/reception control circuit 115 provides protection so that amplitude pulses are not input to the reception processing unit 120 at the time of transmission. The ultrasonic transducer elements 12 receive reception waves of the ultrasonic echoes of the transmitted ultrasonic waves (hereinafter, reception waves) at the same frame rate as at the time of transmission, and the transmission/reception control circuit 115 allows the resultant signals (reception signals) to pass through to the reception processing unit 120.

The reception processing unit 120 acquires the reception signals, and performs reception processing. The reception processing unit 120 is primarily provided with a reception delay circuit 121, a switching circuit 122, a phasing and adding circuit 123, transfer units 124 and 125, an area-of-interest setting unit 126, and a reception control unit 127.

The reception delay circuit 121 applies a delay of delay time $D_m$ to the signal received by each channel, such that the signals received by the respective channels are in phase. Since the reflective wave from a certain reflector spreads spherically, the reception delay circuit 121 applies a delay time such that arrival time at the respective vibrators is the same, and adds the reflective waves together taking into account the delay time.

In the case where there are a total of M channels, an output signal $X_m$ of the mth channel is derived by equation (1). Also, the output signal of each channel is represented by equation (2) when expressed in vector notation. Here, $x_m$ is the reception signal of the mth channel, and n indicates the sample number (i.e., depth in the image).

$$X_m = x_m[n - D_m[n]] \qquad (1)$$

$$X[n] = \begin{bmatrix} x_1[n - D_1[n]] \\ x_2[n - D_2[n]] \\ \vdots \\ x_M[n - D_M[n]] \end{bmatrix} \qquad (2)$$

Figure 6:
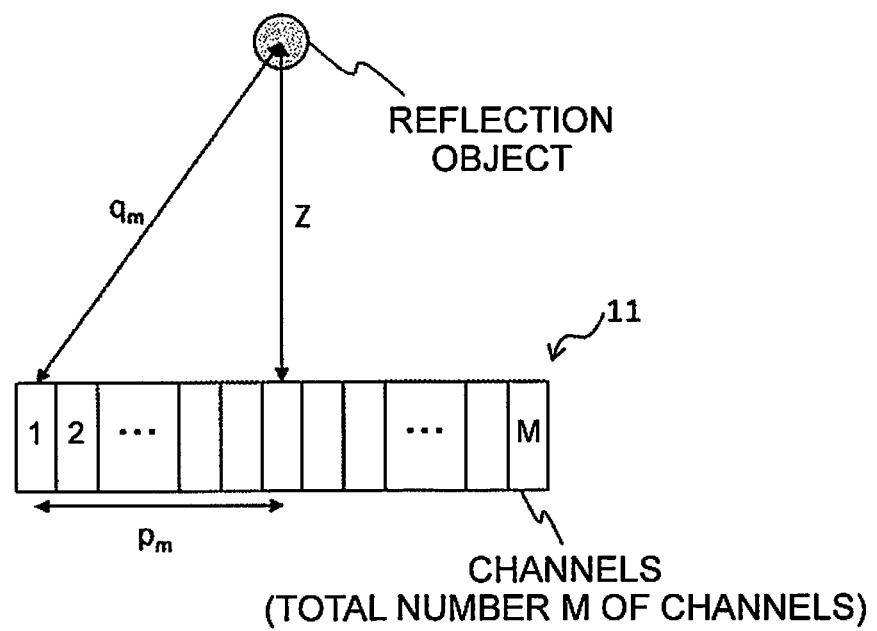
FIG. 6 illustrates a signal delay at each channel.

As shown in FIG. 6, the ultrasonic wave reflected from a reflection object (object) that is located in a depth direction Z from the ultrasonic transducer device 11 arrives at each channel as a spherical wave. Accordingly, the time taken for the reflection signal to arrive at the element of each channel is determined by a linear distance $q_m$ from the reflection object to the channel, with the ultrasonic wave taking longer to arrive as the distance of the element from the reflection object increases. An arrival time $D'_m$ for each element is derived geometrically as shown in equation (3), and is determined by a position $p_m$ of the ultrasonic transducer element 12 in the ultrasonic transducer device 11 and a depth distance Z. c is the sound velocity (fixed value). This arrival time $D'_m$ for each element is converted for use into a delay time $D_m$ from the start of reception.

$$q_m = \sqrt{p_m^2 + Z^2}$$

$$D'_m = q_m/c \qquad (3)$$

The reception delay circuit 121 converts the reception wave (analog signal) of each channel resulting from the delay time $D_m$ being applied to the received signal, and performs filtering on the reception signal using a bandpass filter to removes noise.

The switching circuit 122 outputs, to the transfer unit 125, reception signals output from the reception delay circuit 121, with respect to data forming the basis of an image to be displayed in the area set as the area of interest by the area-of-interest setting unit 126 (discussed in detail later). The switching circuit 122 outputs, to the phasing and adding circuit 123, reception signals output from the reception delay circuit 121, with respect to data forming the basis of an image to be displayed in the area other than the area set as the area of interest by the area-of-interest setting unit 126 (discussed in detail later).

The phasing and adding circuit 123 phases and adds together the reception signals (two-dimensional data) output from the reception delay circuit 121 to obtain one-dimensional data. Specifically, the phasing and adding circuit 123 adds together the signals of the respective channels output from the reception delay circuit 121, using weights computed in advance. Here, the weights computed in advance may be fixed values or may be weights that depend on the number of scan lines, the distance from the object to the channel, or the like. This weight does not, however, vary with the size of the reception signal.

The transfer unit 124 outputs, to the image processing unit 130, the one-dimensional data output from the phasing and adding circuit 123. The transfer unit 125 outputs, to the image processing unit 130, the reception signals output from the reception delay circuit 121.

The area-of-interest setting unit 126 sets the area of interest to within an area in which an image is to be displayed, based on the input received by the area input unit 22 (discussed in detail later). Also, the area-of-interest setting unit 126 computes the frame rate based on the size of the area of interest. Processing by the area-of-interest setting unit 126 will be discussed in detail later.

The reception control unit 127 controls the functional units of the reception processing unit 120. The reception control unit 127 controls the switching circuit 122 and the like based on information relating to the area of interest set by the area-of-interest setting unit 126. Here, information relating to the area of interest is information indicating whether an area of interest has been set (whether there is an area of interest), and information on the position, size and the like of the area of interest in the case where an area of interest has been set. Processing by the reception control unit 127 will be discussed in detail later.

The functions of the reception processing unit 120 can be realized by, for example, an analog front end (AFE) that is constituted by a low noise amplifier (LNA), a programmable gain amplifier (PGA), a filter unit, an analog/digital convertor (A/D convertor), and the like. Also, the functions of the reception control unit 127 can be realized by hardware such as various processors (CPU, etc.) and an ASIC (gate array, etc.), computer programs, or the like.

The image processing unit 130 processes the reception signals output from the reception processing unit 120. The image processing unit 130 primarily includes reception units 131 and 132, an image generation unit 133, a high resolution image generation unit 134, and an image combining unit 135.

The reception unit 131 receives signals transferred from the transfer unit 124. The reception unit 132 receives signals transferred from the transfer unit 125.

The image generation unit 133 generates a B-mode image based on the one-dimensional data transferred from the transfer unit 124. Generation of a B-mode image is already commonly known, and thus a detailed description thereof is omitted.

The high resolution image generation unit 134 performs MVB processing, which is direction-constrained adaptive beamforming, on data forming the basis of the image to be displayed in the area of interest, that is, data transferred from the transfer unit 125, and generates a B-mode image based on the signals obtained from the MVB processing.

Adaptive beamforming is processing that involves dynamically changing the sensitivity characteristics so as to not have sensitivity to unwanted waves, by varying the weight of each channel according to the incoming wave. Even if an ultrasonic beam is transmitted so as to have high sound pressure in a frontal direction, the ultrasonic waves will also reach reflectors that exist in directions other than directly in front, since ultrasonic waves are characterized by spreading spherically. When unwanted waves reflected by reflectors other than the target are received, azimuth resolution deteriorates due to the influence of the unwanted waves. In contrast, adaptive beamforming places a constraint on direction so as to not have sensitivity to unwanted waves, thus enabling the problem of a decrease in azimuth resolution due to unwanted waves to be remedied.

Specifically, the high resolution image generation unit 134 first computes the weight to be applied to signals (output of respective channels) transferred from the transfer unit 125. Here, weight computation will be described.

An output z is the result of multiplying a weight $w_m$ of each channel and a signal $x_m$ obtained from delay processing performed on the channel that is output from reception delay circuit 121 and summing the multiplication results, and is represented by equation (4).

$$z[n] = \sum_{m=1}^{M} w_m[n] x_m[n - D_m[n]] \quad (4)$$

This is represented by equations (5) and (6) when expressed in vector notation. H is a complex conjugate transpose and * is a complex conjugate.

$$z[n] = w[n]^H X[n] \quad (5)$$

$$w[N] = \begin{bmatrix} w_1^*[n] \\ w_2^*[n] \\ \vdots \\ w_M^*[n] \end{bmatrix} \quad (6)$$

A correlation matrix R is represented by equations (7) and (8).

$$R[n] = E[X[n]X[n]^T] \quad (7)$$

$$E[|z[n]|^2] = w[n]^H R[n] w[n] \quad (8)$$

In order to compute a weight that minimizes the variance of z[n] in equations (7) and (8), conditional minimization problems such as shown in equations (9) and (10) are solved to derive the weight as shown in equation 11)

$$\min_{w[n]} w[n]^H R[n] w[n] \quad (9)$$

$$w[n]^H a = 1 \quad (10)$$

$$w[n] = \frac{R[n]^{-1} a}{a^H R[n]^{-1} a} \quad (11)$$

Here, a is a steering vector. In the present embodiment, the direction is 0 degrees since phasing has already being performed. Accordingly, a can be set to 1. The high resolution image generation unit 134 then adds together the signals of the respective channels using the computed weights.

Also, the high resolution image generation unit 134 performs absolute value (rectification) processing on the signal obtained from the adding, and thereafter performs processing with a low-pass passage filter and extracts an unmodulated signal. Also, the high resolution image generation unit 134 performs log compression on the extracted unmodulated signal, and converts the form of expression of the signal, so as to more easily confirm the maximum and minimum signal strengths of reception signals at the same time.

The high resolution image generation unit 134 then adds a direct current component to the log-compressed input signal, and multiplies the log-compressed input signal by a given number.

Furthermore, the high resolution image generation unit 134 corrects the degree of amplification (brightness) according to depth, and acquires an image having uniform brightness across the entire screen. Note that the processing performed after adding together the signals of the respective channels, out of the processing that is performed by the high resolution image generation unit 134, is the same as the processing that is performed by the image generation unit 133.

The image combining unit 135 combines the image generated by the image generation unit 133 and the image generated by the high resolution image generation unit 134. For example, the image combining unit 135 places the image generated by the high resolution image generation unit 134 within the area of interest set by the area-of-interest setting unit 126, and places the image generated by the image generation unit 133 in the remaining area to thus generate a single image. Also, the image combining unit 135 performs scanning conversion on the combined image. For example, the image combining unit 135 converts line signals into image signals by interpolation processing such as bilinear interpolation, and outputs the converted image signals to the display unit 21. An image is thereby displayed on the display unit 21.

Note that the functions of the image processing unit 130 can be realized by hardware such as various processors (CPU, etc.) and an ASIC (gate array, etc.), computer programs, or the like.

Also, an area input unit 22 is provided in the ultrasonic measurement apparatus main body 20. The area input unit 22 is a touch panel, for example, and is provided so as to be overlaid on the display unit 21. The area input unit 22 receives input for changing the information showing the area of interest, based on the information showing the area of interest displayed on the display unit 21. Here, information showing the area of interest is information relating to the position, size, shape or the like of the area of interest. Note that the area input unit 22 is not limited to a touch panel, and input means of various forms, such as a keyboard or a mouse, can be used.

Figure 7A:
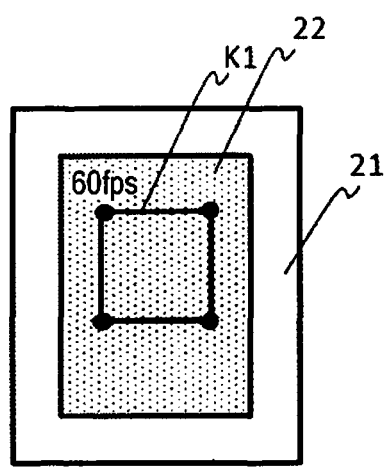
FIGS. 7A and 7B show exemplary information indicating an area of interest that is displayed on a display unit.
Figure 7B:
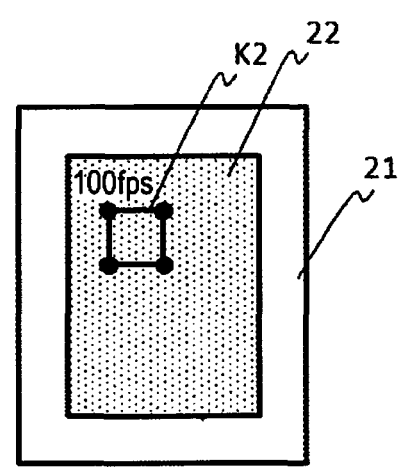

FIGS. 7A and 7B show exemplary information indicating areas of interest for display on the display unit 21. In FIGS. 7A and 7B, the hatched area is the area in which images are displayed. When information showing the area of interest is displayed, an image may be or may not be displayed in the hatched area. That is, information showing the area of interest may be overlaid and displayed on an image, or may be displayed instead of an image.

In the state shown in FIG. 7A, a frame K1 showing the position and size of the area of interest and the text "60 fps" which is the frame rate in the case where the area of interest has the position and size of the frame K1 are displayed on the display unit 21 as information showing the area of interest. A cursor (shown with a black dot) for inputting coordinates is displayed in the four corners of the frame K1 in FIG. 7A. Information showing the area of interest is changed when a cursor position change instruction is input by the user from the area input unit 22.

FIG. 7B shows a state in which the cursor has been moved using the area input unit 22 from the state that is shown in FIG. 7A, and information showing the area of interest, which, here, is the size of the frame showing the position and size of the area of interest, has been changed. In the state that is shown in FIG. 7B, the frame K2 showing the position and size of the area of interest and the text "100 fps" which is the frame rate in the case where the area of interest has the position and size of K2 are displayed on the display unit 21. In this way, as a result of the area of interest becoming smaller, the user can be notified that the frame rate increases. The user can thus be notified that the frame rate will increase as a result of the size of the area of interest being reduced. Conversely, the user is notified that the frame rate will decrease, when the size of the area of interest is increased.

The user is thus able to select a desired frame rate. Note that the frame rate that depends on the area of interest is computed by the area-of-interest setting unit 126 based on the output from the area input unit 22 (discussed in detail later).

By adopting such a configuration, the user is able to select the position, size, shape and the like of the area of interest. Also, since the size of the image and the size of the area of interest can be compared, the user is able to easily select the position, size, shape and the like of the area of interest. Furthermore, by displaying information showing the area of interest so as to be overlaid on the B-mode image, the user is able to appropriately select the area of interest.

Note that the area input unit 22 is also able to input the position and size of the area of interest in the form of a frame, and to input the position of the area of interest by inputting the center coordinates of the area of interest. In the case of inputting the center coordinates of the area of interest, the area-of-interest setting unit 126, upon the shape of the area of interest being input via the area input unit 22 or the like, acquires the input shape, and computes the position and size of the area of interest (discussed in detail later).

The frame and frame rate showing the position and size of the area of interest are displayed on the display unit 21 by the display control unit 140. A configuration may be adopted in which the display control unit 140, upon a cursor for inputting coordinates being selected using the area input unit 22, displays two lines that pass through the cursor and are parallel to the x direction (widthwise direction in FIGS. 7A and 7B) and the z direction (lengthwise direction in FIGS. 7A and 7B) on the display unit 21. Also, the display control unit 140 may display two lines that are parallel to the x direction and the z direction on the display unit 21, for use in inputting the cursor position. In this case, when the two lines are moved using the area input unit 22, the area input unit 22 receives input of a position where the two lines intersect as the position of the cursor. Since the functions of the display control unit 140 are commonly known, description thereof is omitted.

Note that although, in the present embodiment, the area input unit 22 inputs information showing the area of interest based on information showing the area of interest displayed on the display unit 21, the method by which the area input unit 22 inputs information showing the area of interest is not limited thereto. For example, the area input unit 22 may input information showing the area of interest, in a state where an image is displayed on the display unit 21 and information showing the area of interest is not displayed. Also, the area input unit 22 may input information showing the area of interest, in a state where nothing is displayed on the display unit 21.

Although the main configuration of the ultrasonic imaging apparatus 1 has been described above in describing the features of the present embodiment, the configuration of the ultrasonic imaging apparatus 1 is not limited to the above configuration. The instant invention is not restricted by the classification method or names of the constituent elements. The configuration of the ultrasonic imaging apparatus 1 can also be classified into more constituent elements according to the processing content. One constituent element can also be classified so as to execute more processing. Also, the processing of each constituent element may be executed by one piece of hardware or may be executed by multiple pieces of hardware.

In particular, with the ultrasonic imaging apparatus 1 described above, the image processing unit 130 is provided in the ultrasonic measurement apparatus main body 20, but the image processing unit 130 may be provided in the ultrasonic probe 10. Also, with the ultrasonic imaging apparatus 1 described above, the reception processing unit 120 was provided in the ultrasonic probe 10, but the reception processing unit 120 may be provided in the ultrasonic measurement apparatus main body 20. Also, the phasing and adding circuit 123 may be provided between the reception unit 131 and the image generation unit 133 in the image processing unit 130, rather than in the reception processing unit 120.

Figure 8:
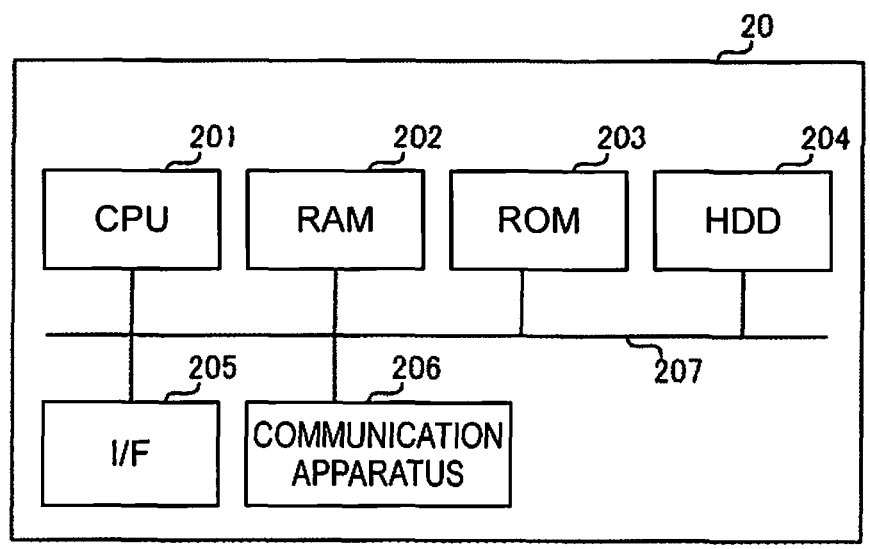
FIG. 8 shows an exemplary schematic configuration of an ultrasonic measurement apparatus main body.

FIG. 8 is a block diagram showing an exemplary schematic configuration of at least a portion of the ultrasonic measurement apparatus main body 20. As shown in the diagram, the ultrasonic measurement apparatus main body 20 is provided with a central processing unit (CPU) 201 that is an arithmetic device, a random access memory (RAM) 202 that is a volatile storage device, a read only memory (ROM) 203 that is a nonvolatile storage device, a hard disk drive (HDD) 204, an interface (I/F) circuit 205 for connecting other units, a communication apparatus 206 that performs communication with external devices, and a bus 207 that connects these constituent elements with each other.

Each of above functional units is realized by the CPU 201 reading out a predetermined program stored in the ROM 203 to the RAM 202 and executing the read program. Note that the predetermined programs may, for example, be installed in the ROM 203 in advance, or may be downloaded from a network via the communication apparatus 206 and installed or updated.

Next, processing by the ultrasonic imaging apparatus 1 of the present embodiment having the above configuration will be described.

Figure 9:
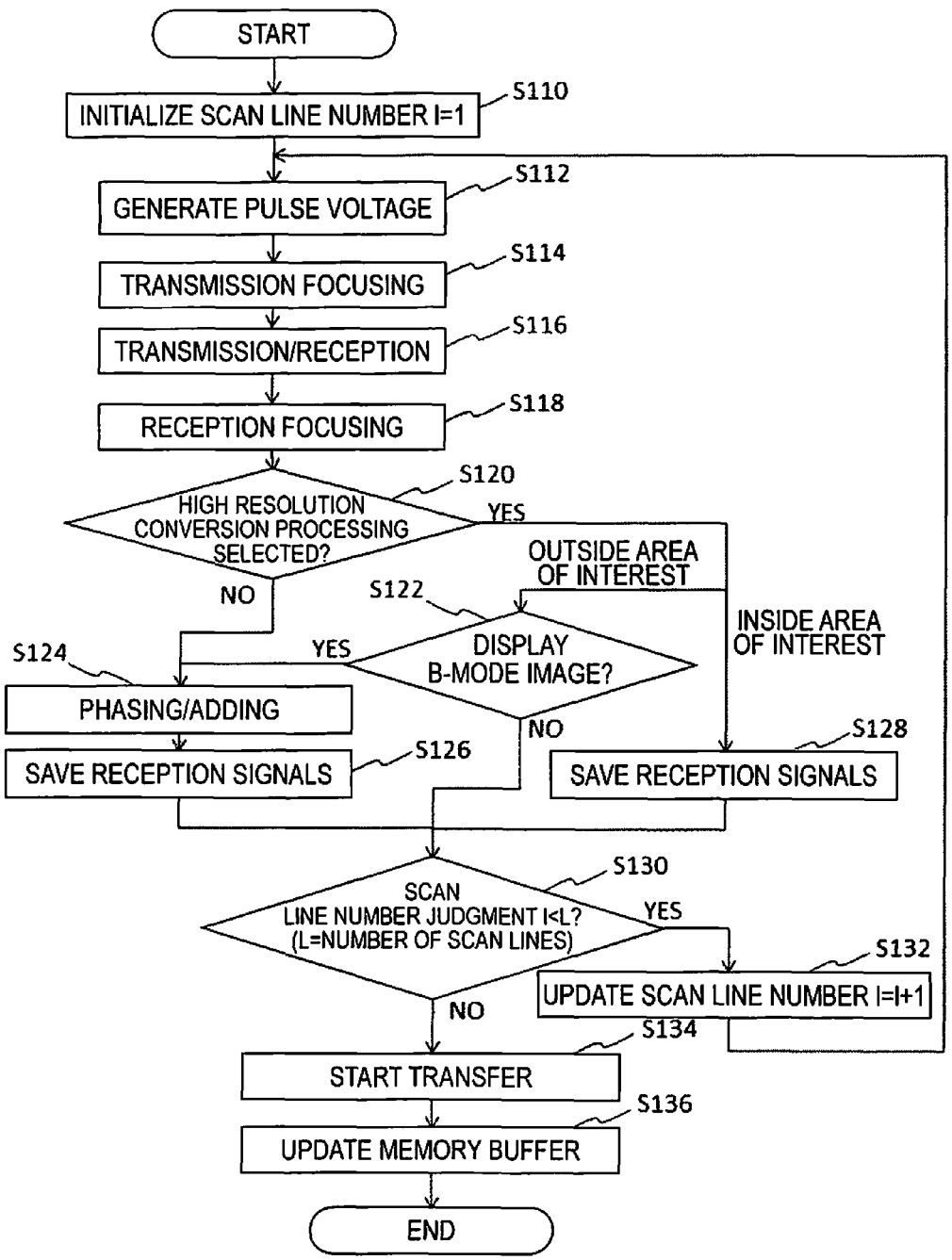
FIG. 9 is a flowchart showing the flow of processing by an ultrasonic probe 10.

FIG. 9 is a flowchart showing the flow of processing by the ultrasonic probe 10.

The reception unit 127 initializes a scan line number l which is a number showing the line for generating an image to 1 (l=1) (step S110). The scan line number l is a number showing one of the ultrasonic transducer element groups UG1 to UG64 constituting an ultrasonic transducer device such as shown in FIG. 3. For example, the scan line number l of an element group provided at a given end, which, here, is the ultrasonic transducer element group UG1, is set to 1. Also, the scan line number l of the element group that is adjacent to the element group having the scan line number 1, which, here, is the ultrasonic transducer element group UG2, is set to 2. A scan line number l is assigned to all the element groups in this way. The relationship between the ultrasonic transducer element groups UG1 to UG64 and the scan line number l can be stored in a memory such as ROM.

The reception unit 127 then performs transmission of an ultrasonic pulse from each channel corresponding to the channel having the scan line number l initialized at step S110 or the scan line number l updated at step S132 which will be discussed later, via the transmission/reception control circuit 115 (steps S112 to S116). For example, the channels at the time of the scan line number 1 are the ultrasonic transducer element groups UG1 to UG8, and the channels at the time of the scan line number 2 are the ultrasonic transducer element groups UG2 to UG9.

Specifically, the transmission pulse generator 111 generates a pulse voltage for transmitting an ultrasonic pulse having a frequency f (f can take an arbitrary value) (step S112). The transmission delay circuit 113 performs transmission focusing control (step S114), and the ultrasonic transducer elements 12 emit ultrasonic beams corresponding to the pulse voltage generated at step S112 toward the object (step S116).

Next, the transmission/reception control circuit 115 performs transmission/reception changeover processing. The ultrasonic transducer elements 12 receive the reception waves that come back as a result of the emitted ultrasonic beams being reflected by the object, and pass the received signals to the reception processing unit 120 (step S116).

The reception delay circuit 121 applies a delay of a predetermined delay time to the reception wave of each channel, so that the signals received by the respective channels are in phase (step S118).

The reception control unit 127 judges whether high resolution conversion processing has been selected by the area-of-interest setting unit 126, that is, whether the area-of-interest setting unit 126 has set an area of interest based on input from the area input unit 22 (step S120).

FIGS. 10A to 10F show modes of the area of interest, with the portion that is hatched with lines (area X in the diagram) being an area in which the area of interest is set, the portion that is hatched with dots (area Y in the diagram) being an area in which the area of interest is not set and in which an B-mode image is displayed, and the area that is not hatched (area Z in the diagram) being an area in which an area of interest is not set and a B-mode image is not displayed.

FIGS. 10A to 10E are modes for displaying a high resolution image in the area of interest, and displaying a B-mode image in the remaining area.

In FIG. 10A, a band-like area of interest is set along the scan line. This facilitates the switching of processing which will be discussed later. In FIG. 10B, a rectangular area of interest is set in a middle portion of the image display area. This enables setting of an area of interest having a minimum size. In FIGS. 10C and 10D, a band-like area of interest is set in a direction that is orthogonal to the scan line. This facilitates the switching of processing which will be discussed later. In FIG. 10E, a circular area of interest is set in a middle portion of the image display area. This enables setting of an area of interest having a minimum size.

Note that although a rectangular area of interest is set in FIG. 10B, the area of interest may be square or trapezoidal in shape. Also, although a circular area of interest is set in FIG. 10E, the area of interest may be elliptical in shape.

In FIG. 10F, a rectangular area of interest is set in a middle portion of the image display area similarly to FIG. 10B, although this is an mode in which a high resolution image is displayed in the area of interest, and a B-mode image is not displayed in the remaining area. Note that the position and shape of the area of interest in a configuration for displaying only a high resolution image are not limited thereto. The configurations of the various areas of interest shown in FIGS. 10A to 10E can also be configured to display only a high resolution image. Whether or not a B-mode image is to be displayed in the area other than the area of interest can be input to the area-of-interest setting unit 126 via an input unit such as the area input unit 22.

Next, the method of setting an area of interest such as shown in FIGS. 10A to 10F when information showing the position of the area of interest (center coordinates of the area of interest) is input from the area input unit 22 will be described. In this case, the area-of-interest setting unit 126 sets the size of the area of interest based on the frame rate. The frame rate may be a value set in advance or may be a value input via the area input unit 22 or the like. Note that since the ultrasonic propagation time is extremely short, the ultrasonic propagation time is not taken into consideration in the following description.

If an area of interest is not set, that is, if a B-mode image is displayed for the entire image, a time T1 for generating a single image is represented by equation (12). The total pixel count of an image is given as z pixels in the lengthwise direction and x pixels the widthwise direction. Also, the time taken to generate a 1-pixel image in B-mode is given as a seconds.

$$T1 = x \times z \times a \text{ [sec]} \tag{12}$$

If the whole image is set as an area of interest, that is, if a high resolution image is displayed for the entire image, a time T2 taken to generate a single image is represented by equation (13). Note that time taken to generate 1-pixel of a high resolution image is given as b (a<b) seconds.

$$T2 = x \times z \times b \text{ [sec]} \tag{13}$$

As shown in FIGS. 10A to 10E, in the case where a B-mode image and a high resolution image are combined, a time T3 taken to generate a single image is represented by equation (14), where A pixels is the pixel count for displaying the B-mode image, and B pixels is the pixel count for displaying the high resolution image. Note that $x \times z = A + B$.

$$\begin{aligned} T3 &= (x \times z - B) \times a + (x \times z - A) \times b \\ &= (x \times z - B)a + (x \times z - (x \times z - B))b \\ &= (x \times z)a - B(a - b) \text{ [sec]} \end{aligned} \tag{14}$$

Accordingly, in order to set the frame rate in the case where a B-mode image and a high resolution image are combined to a frame rate at or above an arbitrary frame rate, that is, in order to achieve image generation in the case where a B-mode image and a high resolution image are combined at a frame rate at or above an arbitrary frame rate, high resolution processing can be performed within the total pixel count B that satisfies the condition of equation (15). Here, t4 is a value obtained by multiplying the time in the case of displaying a B-mode image for the entire image by a number greater than or equal to 1, and the arbitrary frame rate can be shown by 1/T4.

$$T3 \leq T4 \tag{15}$$

The pixel count B of the area (area of interest) in which high resolution processing can be performed while satisfying the frame rate that is desired by the user is thereby derived. Once the pixel count B is derived, the area-of-interest setting unit 126 is able to specify the position and size of the area of interest from the center coordinates and the pixel count B of the area of interest, for example. Hereinafter, the method by which the area-of-interest setting unit 126 specifies the position and size of the area of interest from the center coordinates and the pixel count B of the area of interest will be described.

In the case of FIGS. 10A to 10D, the area-of-interest setting unit 126 derives the coordinates of the four corners of the area of interest, based on the pixel count B of the area (area of interest) in which high resolution processing is performed. The area-of-interest setting unit 126 is able to set the central point of the area of interest to coordinates input by the area input unit 22 or to the center of the image, for example. Also, the area-of-interest setting unit 126 is able to derive the coordinates of the four corners of the area of interest, based on the coordinates of the central point of the area of interest and the pixel count B of the area of interest. The area-of-interest setting unit 126 specifies the position and size of the area of interest using the coordinates of the four corners.

Figure 11:
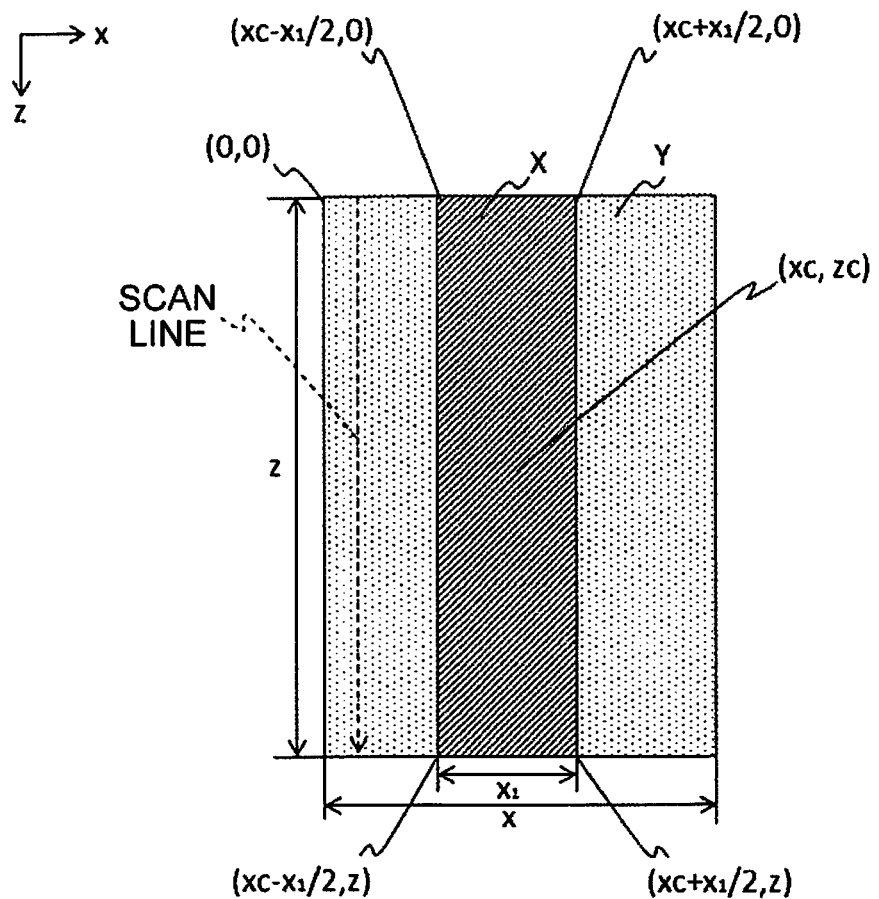
FIG. 11 shows specification of the position and size of the area of interest in the case of setting a band-like area of interest.

FIG. 11 shows specification of the position and size of area of interest in the case of setting a band-like area of interest such as shown in FIG. 10A. The area-of-interest setting unit 126 is able to compute $x_1$ as B/z. The area-of-interest setting unit 126 is able to compute the coordinates of the four corners of the area of interest as $(xc-x_1/2, 0)$, $(xc+x_1/2, 0)$, $(xc-x_1/2, z)$ and $(xc+x_1/2, z)$, where the center coordinates of the area of interest are given as (xc, zc).

Figure 12:
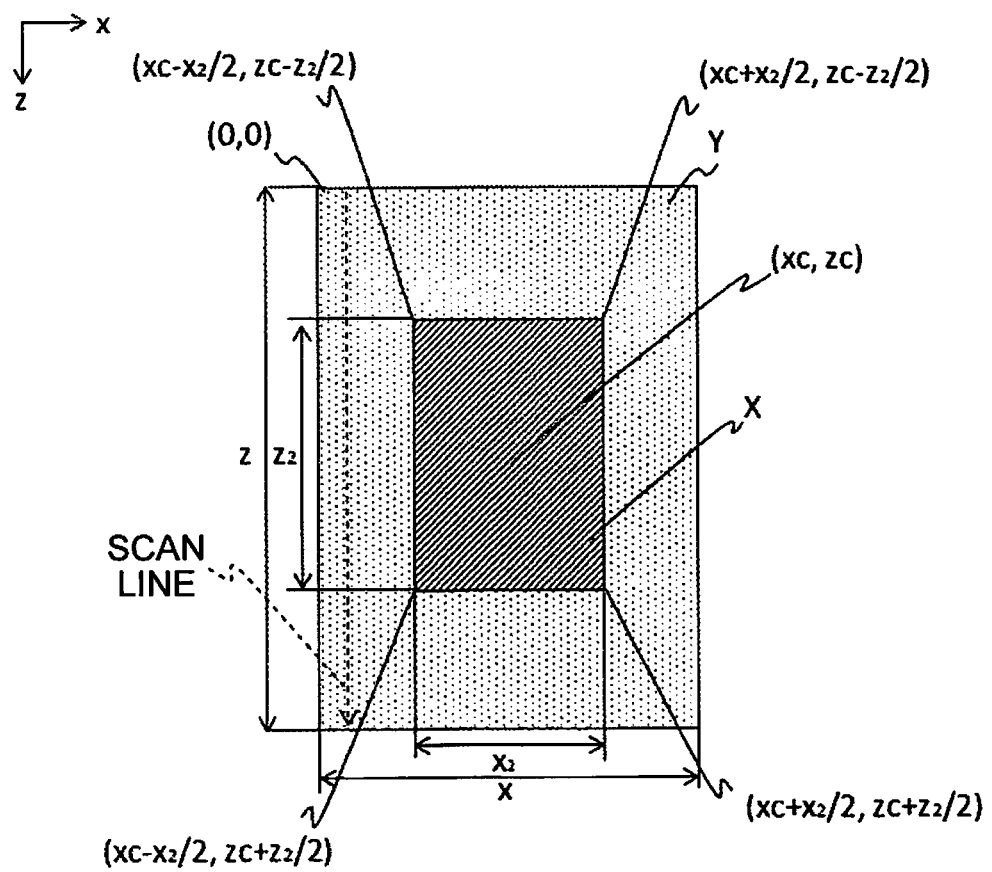
FIG. 12 shows specification of the position and size of the area of interest in the case of setting a rectangular area of interest.

FIG. 12 shows specification of the position and size of the area of interest in the case of setting a rectangular area of interest such as shown in FIG. 10B. The area-of-interest setting unit 126 is able to compute $x_2$ and $z_2$ such that $x_2 \times z_2$ satisfies B, where the aspect ratio $(x_2:z_2)$ of the area of interest is the same as the aspect ratio (x:z) of the entire image. The area-of-interest setting unit 126 computes the coordinates of the four corners of the area of interest as $(xc-x_2/2, zc-z_2/2)$, $(xc+x_2/2, zc-z_2/2)$, $(xc-x_2/2, zc+z_2/2)$ and $(xc+x_2/2, zc+z_2/2)$, where the center coordinates of the area of interest are given as (xc, zc).

Figure 13:
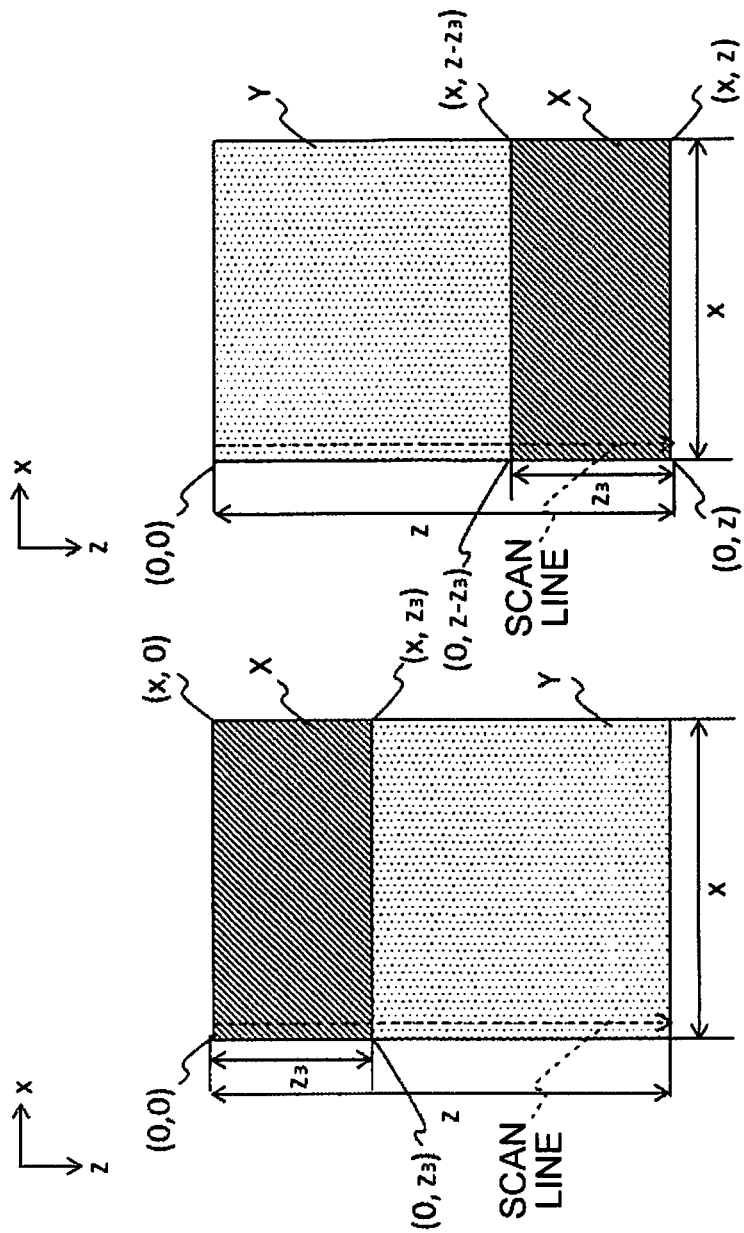
FIGS. 13A and 13B show specification of the position and size of the area of interest in the case of setting a band-like area of interest.

FIG. 13 shows specification of the position and size of the area of interest in the case of setting a band-like area of interest such as shown in FIGS. 10C and 10D. The area-of-interest setting unit 126 is able to compute $z_3$ as B/x. Accordingly, the area-of-interest setting unit 126 is able to compute the coordinates of the four corners of the area of interest in the case of FIG. 10C as (0, 0), (x, 0), (0, $z_3$) and (x, $z_3$). Also, the area-of-interest setting unit 126 is able to compute the coordinates of the four corners of the area of interest in the case of FIG. 10D as (0, z–$z_3$), (x, z–$z_3$), (0, z) and (x, z).

Figure 14:
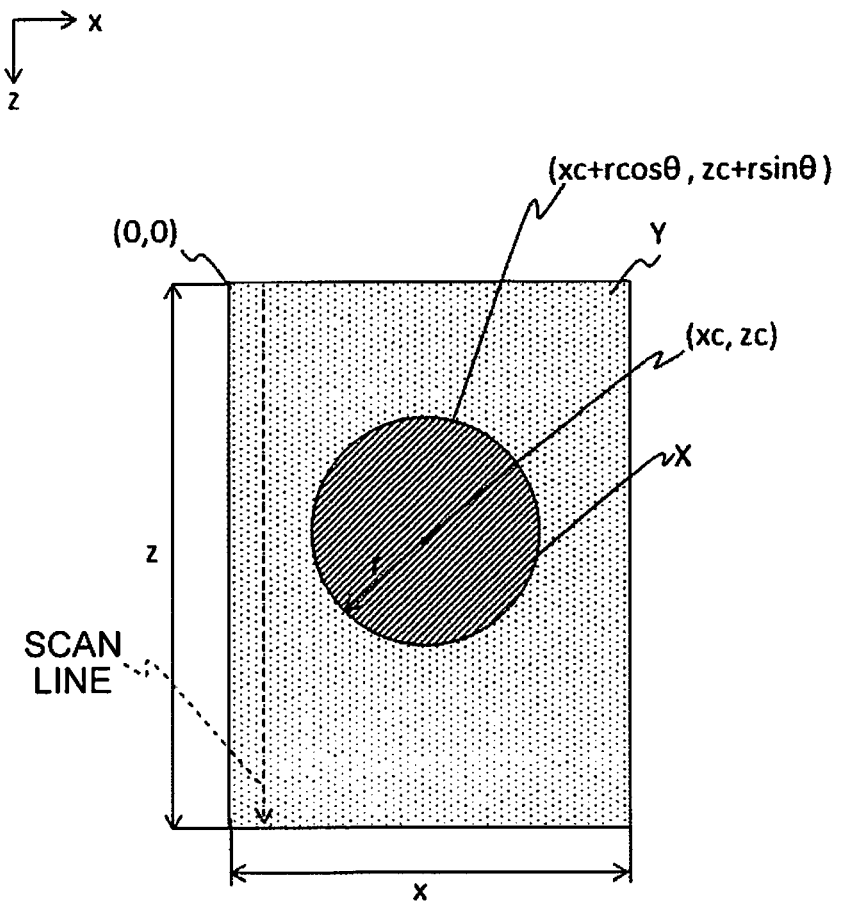
FIG. 14 shows specification of the position and size of the area of interest in the case of setting a circular area of interest.

FIG. 14 shows specification of the position and size of the area of interest in the case of setting a circular area of interest such as shown in FIG. 10E. The area-of-interest setting unit 126 computes the radius and the coordinates of the periphery of the area of interest, and saves the computed radius and coordinates in a memory (not shown) together with the center coordinates. The area-of-interest setting unit 126 specifies the position and size of the area of interest using the center coordinates and the radius.

In the case of FIG. 10E, the area-of-interest setting unit 126 is able to compute r for which $\pi r^2$ satisfies B, as shown in FIG. 14. The area-of-interest setting unit 126 is able to compute the coordinates of the periphery of the area of interest as $(xc + r \cos \theta, zc + r \sin \theta)$, where the center coordinates of the area of interest are given as (xc, zc). Here, $\theta$ is an angle formed by a line that passes through the coordinates (xc, zc) and lies parallel to the x-axis.

Note that, in the case where the area of interest is elliptical in shape, a configuration can be adopted in which the major diameter and the minor diameter are derived, and the coordinates of the periphery of the area of interest are derived based on the major diameter and the minor diameter.

Next, the case of displaying only a high resolution image, as shown in FIG. 10F, will be described. When the pixel count for displaying a high resolution image is given as B pixels, high resolution processing can be performed in a range of the total pixel count B that satisfies the condition of equation (16).

$$B \times b \leq x \times z \times a \tag{16}$$

The area-of-interest setting unit 126 is then able to compute $x_4$ and $z_4$ for the pixel count $x_4 \times z_4$ of the area of interest that satisfies B, where the aspect ratio ($x_4:z_4$) of the area of interest is the same as the aspect ratio ($x:z$) of the entire image. The area-of-interest setting unit 126 is able to compute the coordinates of the four corners of the area of interest as ($xc-x_4/2$, $zc-z_4/2$), ($xc+x_4/2$, $zc-z_4/2$), ($xc-x_4/2$, $zc+z_4/2$) and ($xc+x_4/2$, $zc+z_4/2$), where the center coordinates of the area of interest are given as ($xc$, $zc$).

A method of setting the area of interest when the center coordinates of the area of interest are input from the area input unit 22 was described above. In contrast, when the position and size of the area of interest are input from the area input unit 22, the coordinates of the four corners of the area of interest, the radius and the like are input from the area input unit 22. In this case, the area-of-interest setting unit 126 derives the frame rate based on equation (14). In the case where a frame rate that is desired by the user is set, the area-of-interest setting unit 126 may restrict the size of the area of interest that can be input, such that the frame rate that is derived based on equation (14) will be greater than or equal to the frame rate that is desired by the user.

The area-of-interest setting unit 126 saves the scan number and sampling number corresponding to the derived coordinates of the area of interest in a memory (not shown). The relationship of the coordinates of a given position in an image with the scan number and sampling number is saved in advance in the memory, for example, and the area-of-interest setting unit 126 is able to derive the scan number and sampling number corresponding to the coordinates of the area of interest based on this information.

Returning to the description of FIG. 9, if high resolution conversion processing is not selected, that is, if an area of interest is not set (NO at step S120), the switching circuit 122, in accordance with an instruction of the reception control unit 127, outputs the signals that are output from the reception delay circuit 121 to the phasing and adding circuit 123. The phasing and adding circuit 123 phases and adds together the reception signals (two-dimensional data) output from the reception delay circuit 121 to obtain one-dimensional data (step S124).

Thereafter, the phasing and adding circuit 123 stores the reception signal in a buffer memory (not shown) provided in RAM (not shown) or the like (step S126).

If, in the case where high resolution conversion processing is selected, that is, in the case where an area of interest is set (YES at step S120), the position currently being processed is within the high resolution conversion processing area, the reception control unit 127 switches the switching circuit 122 to the transfer unit 125 side, and stores the reception signals output from the reception delay circuit 121 in a buffer memory (not shown) provided in RAM (not shown) or the like (step S128). Also, if, in the case where an area of interest is set (YES at step S120), the position currently being processed is not within the high resolution conversion processing area, the reception control unit 127 judges whether to display a B-mode image in the area other than the area of interest (step S122). Hereinafter, how the reception control unit 127 determines whether the position currently being processed is within the high resolution conversion processing area will be described in relation to the modes of the areas of interest shown in FIGS. 11 to 14.

For example, in the case shown in FIG. 11, the reception control unit 127 determines that the position currently being processed is within the high resolution conversion processing area if the current scan line number l is a scan number corresponding to an x-coordinate from $xc-x_1/2$ to $xc+x_1/2$, and determines that the position currently being processed is not within the high resolution conversion processing area if this is not the case.

In the case shown in FIG. 12, the reception control unit 127 determines that the position currently being processed is not within the high resolution conversion processing area, if the current scan line number l is not a scan number corresponding to an x-coordinate from $xc-x_2/2$ to $xc+x_2/2$. Also, the reception control unit 127 determines that the position currently being processed is within the high resolution conversion processing area if the sampling number corresponds to a z-coordinate from $zc-z_2/2$ to $zc+z_2/2$, in the case where the current scan line number l is a scan number corresponding to an x-coordinate from $xc-x_2/2$ to $xc+x_2/2$, and determines that the position currently being processed is not within the high resolution conversion processing area if this is not the case. In the cases shown in FIGS. 13A and 13B, the reception control unit 127 determines that the position currently being processed is within the high resolution conversion processing area in the case of FIG. 13A, if the sampling number corresponds to a z coordinate from 0 to $z_3$ for any scan line number, and determines that the position currently being processed is not within the high resolution conversion processing area if this is not the case. Also, the reception control unit 127 determines that the position currently being processed is within the high resolution conversion processing area in the case of FIG. 13B, if the sampling number corresponds to a z coordinate from $z-z_3$ to z for any scan line number, and determines that the position currently being processed is not within the high resolution conversion processing area if this is not the case.

In the case shown in FIG. 14, the reception control unit 127 determines that the position currently being processed is within the high resolution conversion processing area, in the case where the coordinates (X, Z) on the image that are designated by the current scan line number l and sampling number satisfy $(X-xc)^2+(Z-zc)^2 \leq r^2$, and determines that the position currently being processed is not within the high resolution conversion processing area if this is not the case.

In the case of displaying a B-mode image in the area other than the area of interest when the position currently being processed is not within the high resolution conversion processing area (YES at step S122), the reception control unit 127 switches the switching circuit 122 to the phasing and adding circuit 123 side. The phasing and adding circuit 123 then phases and adds together the reception signals (two-dimensional data) output from the reception delay circuit 121 to obtain one-dimensional data (step S124), and the phasing and adding circuit 123 stores the reception signals in a buffer memory (not shown) provided in RAM (not shown) or the like (step S126).

The case of not displaying a B-mode image in the area other than the area of interest when the position currently being processed is not within the high resolution conversion processing area (NO at step S122) is shown in FIG. 10F, for example. In this case, the reception control unit 127 advances the processing to step S130, without storing the reception signals in the buffer memory (not shown).

Next, the reception control unit 127 judges whether the scan line number l showing the line for generating an image is less than the number L of scan lines (step S130). The number L of scan lines depends on the number of ultrasonic transducer element groups UG1 to UG64 constituting an ultrasonic transducer device 11 such as shown in FIG. 3.

If the scan line number l is less than the number L of scan lines (YES at step S130), the reception control unit 127 adds 1 to the current scan line number l to update the scan line number l, and returns the processing to step S112 (step S132).

If the scan line number l is not less than the number L of scan lines (NO at step S130), the scan line number l matches the number L of scan lines, that is, transmission and reception of ultrasonic pulses has ended for all the lines. In this case, the reception control unit 127 starts transfer of the reception signals stored in the buffer memory (not shown) at steps S126 or S128 from the transfer unit 124 or 125 to the image processing unit 130 (step S134), and updates the data of the buffer memory (step S136).

Figure 15:
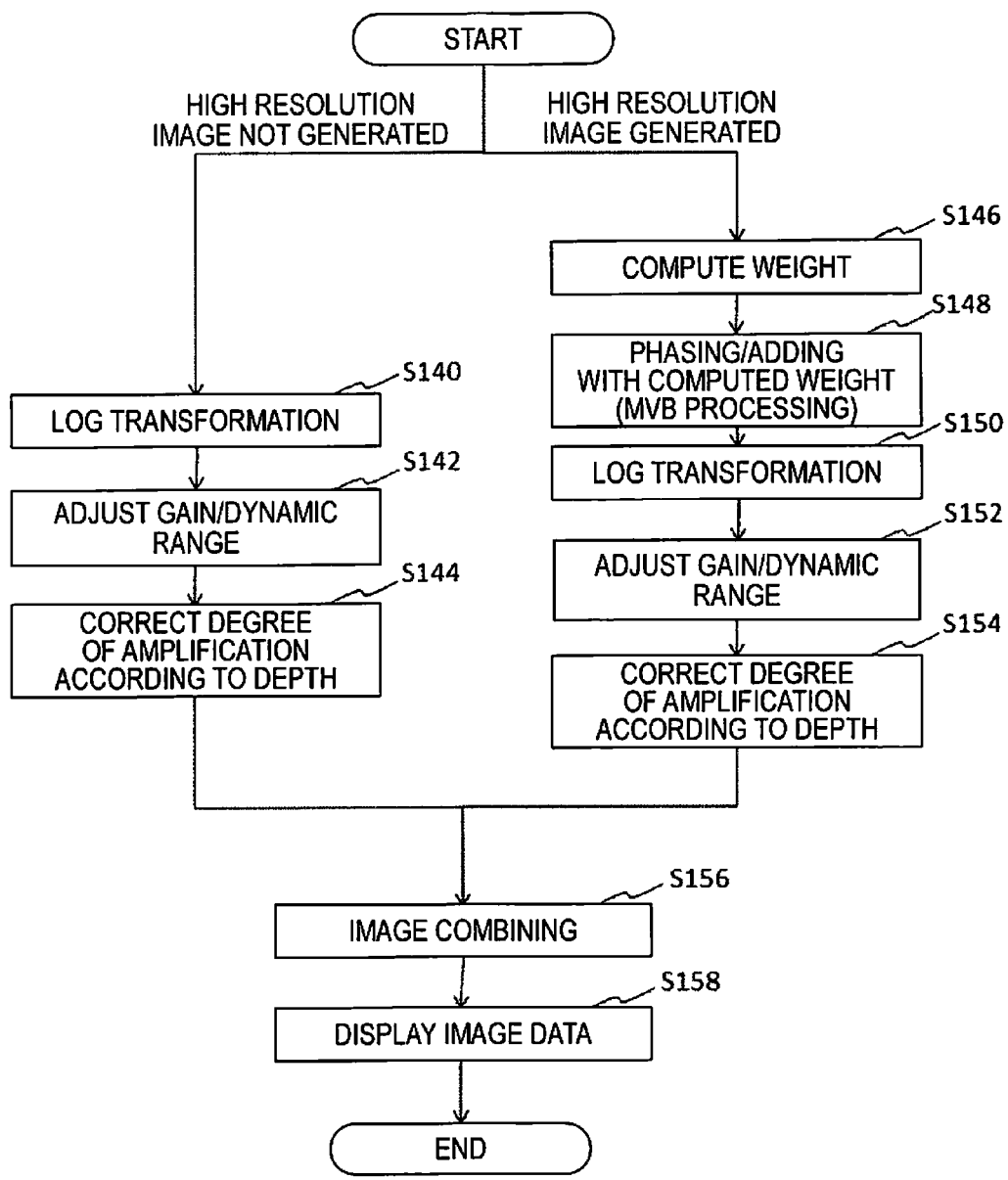
FIG. 15 is a flowchart showing the flow of the processing in an ultrasonic measurement apparatus main body 20.

FIG. 15 is a flowchart showing the flow of the processing in the ultrasonic measurement apparatus main body 20.

Since phasing and adding have already been performed in the case of displaying a normal B-mode image, that is, in the case where reception signals are received by the reception unit 131, the reception unit 131 outputs the reception signals to the image generation unit 133. The image generation unit 133 performs logarithmic transformation on the reception signals (step S140), adjusts the gain and dynamic range (step S142), and corrects the degree of amplification (brightness) according to depth (step S144).

In the case of displaying a high resolution image, that is, in the case where reception signals are received by the reception unit 132, the reception unit 132 outputs the reception signals to the high resolution image generation unit 134. The high resolution image generation unit 134 applies a delay of a predetermined delay time D to the signals received by the channels, and computes a weight to be applied to the reception signal of each channel (step S146). The high resolution image generation unit 134 then adds together the signals of the respective channels using the computed weight (step S148). This ends the MVB processing.

Also, the high resolution image generation unit 134 performs logarithmic transformation on the signals obtained from the MVB processing (step S150), adjusts the gain and dynamic range (step S152), and corrects the degree of amplification (brightness) according to depth (step S154).

The image combining unit 135 then combines the signals generated at step S144 and the signals generated at step S154 to obtain the data of a single image, performs scan conversion on the obtained image data to generate B-mode image data (image data for display), and outputs the generated B-mode image data to the display unit 21 (step S156). The display unit 21 displays the generated image data for display (step S158). This ends the processing shown in FIG. 10.

According to the present embodiment, an increase in processing speed can be achieved together with an increase in resolution, since an area for displaying a high resolution image is set in a portion of whole image.

Since calculation processing needs to be performed for the respective reception signals of each channel, in the case of using adaptive beamforming in order to obtain an image with excellent resolution, huge amounts of data need to be processed. Accordingly, when a high resolution image is generated using adaptive beamforming, there is a problem in that the image updating speed, that is, the frame rate, is restricted by the calculation speed. In contrast, generating a high resolution image only in required portions, as in the present embodiment, enables the frame rate to be increased, that is, a higher frame rate to be achieved.

Also, according to the present embodiment, an image that has undergone high resolution conversion processing that involves a large number of calculations can be displayed in a portion that is focused on, while maintaining the necessary frame rate.

Also, according to the present embodiment, usability can be improved, since a conventional B-mode image can also be displayed. Furthermore, in the case of displaying a B-mode image in an area in which a high resolution image is not displayed, any sense of strangeness felt when viewing the image can be reduced.

Also, according to the present embodiment, the size of the area of interest for generating a high resolution image can be set such that the frame rate does not differ from the frame rate in the case of displaying only a normal B-mode image, even in the case of displaying a high resolution image in the area of interest, enabling usability to be further improved.

Note that, in the present embodiment, linear scanning was described as an example, but the invention can also be applied to convex scanning or sector scanning. In the case of convex scanning or sector scanning, a trapezoidal or fan-shaped area is set as the area of interest, since the beam moves radially. For example, the area-of-interest setting unit 126 derives the coordinates of the four corners of the area of interest by the same method as the case shown in FIG. 10B, and sets the area of interest by connecting these coordinates with straight lines or curved lines. The area-of-interest setting unit 126 is able to derive the scan number and sampling number corresponding to the coordinates of the area of interest based on this information.

Although the invention has been described above using embodiments, the technical scope of the invention is not limited to the scope given in the above embodiments. A person skilled in the art will appreciate that numerous changes and modifications can be made to the embodiments. Also, it is obvious from the claims that configurations to which changes and modifications have been made are included in the technical scope of the invention. Also, the invention is not limited to an ultrasonic measurement apparatus, and can also be provided as an image processing method that is performed in an ultrasonic measurement apparatus, a program that causes an ultrasonic measurement apparatus to perform the image processing method, a storage medium on which the program is stored, or the like.

In particular, although, in the above embodiment, the invention was described taking the ultrasonic imaging apparatus 1 provided with the display unit 21 in the ultrasonic measurement apparatus main body 20 as an example, the display unit 21 need not be provided in the ultrasonic imaging apparatus 1. For example, an apparatus according to the invention may be provided as an ultrasonic measurement apparatus that does not have a display unit and outputs generated image data for display to an external display device.

Also, in the above embodiment, the switching circuit 122 is used to output reception signals to the transfer unit 125 with respect to data forming the basis of an image to be displayed in an area set as the area of interest by the area-of-interest setting unit 126, and to output reception signals to the phasing and adding circuit 123 with respect to data forming the basis of an image displayed in the remaining area. However, the switching circuit 122 is not essential, and reception signals can all be output to the phasing and adding circuit 123 and the transfer unit 125. In this case, the image combining unit 135 can use data that is output from the high resolution image generation unit 134 with respect to the image to be displayed in the area set as the area of interest by the area-of-interest setting unit 126, and can use data that is output from the image generation unit 133 with respect to the image to be displayed in the remaining area.

Also, in the case of using the switching circuit 122, the installation position of the switching circuit 122 is not limited to the above. For example, the switching circuit 122 may be provided downstream of the phasing and adding circuit 123, and output signals from the reception delay circuit 121 and output signals from the phasing and adding circuit 123 may be input to the switching circuit 122. In this case, signals forming the basis of the image that are input to the switching circuit 122 and mode control information (generated by the reception control unit 127) showing the position of the area of interest and the like are transferred from the transfer unit 124 to the reception unit 131 (the transfer unit 125 and the reception unit 132 are not required). The reception unit 131 can output signals forming the basis of the image to the image generation unit 133 and the high resolution image generation unit 134, and the image combining unit 135 can combine the image output from the image generation unit 133 and the image output from the high resolution image generation unit 134 based on the mode control information.

The entire disclosure of Japanese Patent Application Nos. 2013-183798, filed Sep. 5, 2013, and 2014-129971, filed Jun. 25, 2014 are expressly incorporated by reference herein.

What is claimed is:

1. An ultrasonic measurement apparatus comprising:
   an image processing unit that generates an image based on a reception signal obtained by an ultrasonic echo of an ultrasonic wave transmitted toward an object from an ultrasonic element array provided with a plurality of channels being received by the ultrasonic element array; and
   an area-of-interest setting unit that sets an area of interest within a display area in which the generated image is to be displayed, the area of interest being smaller than the display area,
   in response to setting of the area of interest, for reception signals of respective channels among the plurality of channels, the image processing unit performing a high resolution image generation with respect to first data forming a basis of an image to be displayed in the area of interest, and performing a non-high resolution image generation with respect to second data forming a basis of an image to be displayed in a different area other than the area of interest in the display area,
   the image processing unit, as the performing of the high resolution image generation, receiving reception signals for the area of interest, performing a weight calculation to calculate an adaptive weight according to the reception signals, adding by performing phasing output using the adaptive weight and the reception signals, and performing image generation based on the phasing output, the image processing unit, as the performing of the non-high resolution image generation, receiving reception signals for the different area, which have been added together with a predetermined weight that is computed in advance and does not vary based on the reception signals before the image processing unit receives the reception signals for the different area, and performing image generation based on the reception signals which have been added together with the predetermined weight,
   the image processing unit including an image combining unit that combines the image generated by the performing of the high resolution image generation and the image generated by the performing of the non-high image generation.

2. The ultrasonic measurement apparatus according to claim 1,
   wherein the image processing unit derives the weight that depends on the reception signal of each channel, so as to minimize a variance of a result of multiplying the output signal of the channel after a delay time that depends on a linear distance from an object to the channel by the weight that depends on the reception signal of the channel.

3. An ultrasonic imaging apparatus comprising:
   an image processing unit that generates an image based on a reception signal obtained by an ultrasonic echo of an ultrasonic wave transmitted toward an object from an ultrasonic element array provided with a plurality of channels being received by the ultrasonic element array;
   a display unit that displays the generated image;
   an area-of-interest setting unit that sets an area of interest within a display area in which the generated image is to be displayed, the area of interest being smaller than the display area,
   in response to setting of the area of interest, for reception signals of respective channels among the plurality of channels, the image processing unit performing a high resolution image generation with respect to data forming a basis of an image to be displayed in the area of interest, and performing a non-high resolution image generation with respect to data forming a basis of an image to be displayed in a different area other than the area of interest in the display area,
   the image processing unit, as the performing of the high resolution image generation, receiving reception signals for the area of interest, performing a weight calculation to calculate an adaptive weight according to the reception signals, adding by performing phasing output using the adaptive weight and the reception signals, and performing image generation based on the phasing output, the image processing unit, as the performing of the non-high resolution image generation, receiving reception signals for the different area, which have been added together with a predetermined weight that is computed in advance and does not vary based on the reception signals before the image processing unit receives the reception signals for the different area, and performing image generation based on the reception signals which have been added together with the predetermined weight,
   the image processing unit including an image combining unit that combines the image generated by the performing of the high resolution image generation and the image generated by the performing of the non-high image generation.

4. The ultrasonic imaging apparatus according to claim 3, further comprising:
   an area input unit that receives input of an arbitrary point or area on an image displayed on the display unit,
   wherein the area-of-interest setting unit sets the area of interest based on the arbitrary point or area that was input.

5. The ultrasonic imaging apparatus according to claim 4,
   wherein the area input unit receives input of a desired frame rate, the area-of-interest setting unit sets the area of interest to a size that enables image generation at a frame rate at or above the desired frame rate, and as the frame rate increases, the size of the area of interest decreases.

6. The ultrasonic imaging apparatus according to claim 3, wherein the area-of-interest setting unit sets a rectangular, trapezoidal or fan-shaped area as the area of interest, and specifies the rectangular, trapezoidal or fan-shaped area using coordinates of four corners.

7. The ultrasonic imaging apparatus according to claim 3, wherein the area-of-interest setting unit sets a circular or elliptical area as the area of interest, and specifies the circular or elliptical area using center coordinates and a diameter.

8. The ultrasonic imaging apparatus according to claim 4, wherein the display unit displays information showing the set area of interest so as to be overlaid on the generated image or instead of the generated image, the area input unit receives input for changing the information showing the area of interest, and the area-of-interest setting unit sets the area of interest based on the information showing the area of interest with respect to which the change input was received.

9. The ultrasonic imaging apparatus according to claim 3, further comprising:

a phasing and adding circuit that adds together the acquired reception signals with the predetermined weight, with respect to the data forming the basis of the image to be displayed in the different area.

10. An ultrasonic measurement method comprising:

generating, at an image processing unit, an image based on a reception signal obtained by an ultrasonic echo of an ultrasonic wave transmitted toward an object being received;

setting an area of interest within a display area in which the generated image is to be displayed, the area of interest being smaller than the display area;

in response to setting of the area of interest, for reception signals of respective channels among the plurality of channels, performing a high resolution image generation with respect to data forming a basis of an image to be displayed in the area of interest, and performing a non-high resolution image generation with respect to data forming a basis of an image to be displayed in a different area other than the area of interest in the display area, the performing of the high resolution image generation including receiving reception signals for the area of interest, performing a weight calculation to calculate an adaptive weight according to the reception signals, adding by performing phasing output using the adaptive weight and the reception signals, and performing image generation based on the phasing output, and the performing of the non-high resolution image generation including receiving reception signals for the different area, which have been added together with a predetermined weight that is computed in advance and does not vary based on the reception signals before receiving the reception signals for the different area, and performing image generation based on the reception signals which have been added together with the predetermined weight; and combining the image generated by the performing of the high resolution image generation and the image generated by the performing of the non-high image generation.

11. The ultrasonic measurement apparatus according to claim 1, further comprises a switching circuit that switches between a first output and a second output while one frame is generated, while the switching circuit switches to the first output, the switching circuit outputting the first data forming the basis of the image to be displayed in the area of interest such that the image processing unit performs the high resolution image generation with respect to the first data, and while the switching circuit switches to the second output, the switching circuit outputting the second data forming the basis of the image to be displayed in the different area other than the area of interest in the display area such that the image processing unit performs the non-high resolution image generation with respect to the second data.

* * * * *